US011508482B2

(12) United States Patent
Mason et al.

(10) Patent No.: US 11,508,482 B2
(45) Date of Patent: Nov. 22, 2022

(54) SYSTEMS AND METHODS FOR REMOTELY-ENABLED IDENTIFICATION OF A USER INFECTION

(71) Applicant: ROM TECHNOLOGIES, INC., Brookfield, CT (US)

(72) Inventors: Steven Mason, Las Vegas, NV (US); Daniel Posnack, Fort Lauderdale, FL (US); Peter Arn, Roxbury, CT (US); Wendy Para, Las Vegas, NV (US); S. Adam Hacking, Nashua, NH (US); Micheal Mueller, Oil City, PA (US); Joseph Guaneri, Merrick, NY (US); Jonathan Greene, Denver, CO (US)

(73) Assignee: Rom Technologies, Inc., Brookfield, CT (US)

( * ) Notice: Subject to any disclaimer, the term of this patent is extended or adjusted under 35 U.S.C. 154(b) by 0 days.

(21) Appl. No.: 17/379,740

(22) Filed: Jul. 19, 2021

(65) Prior Publication Data
US 2021/0407681 A1 Dec. 30, 2021

Related U.S. Application Data

(63) Continuation of application No. 17/146,694, filed on Jan. 12, 2021, which is a continuation-in-part of
(Continued)

(51) Int. Cl.
*A61B 5/00* (2006.01)
*G16H 50/20* (2018.01)
(Continued)

(52) U.S. Cl.
CPC .............. *G16H 50/20* (2018.01); *A61B 5/01* (2013.01); *A61B 5/1032* (2013.01); *A61B 5/11* (2013.01);
(Continued)

(58) Field of Classification Search
CPC ....... A61B 5/0022; A61B 5/0077; A61B 5/01; A61B 5/1032; A61B 5/1071; A61B 5/11;
(Continued)

(56) References Cited

U.S. PATENT DOCUMENTS

| 59,915 A | 11/1866 | Lallement |
| 363,522 A | 5/1887 | Knous |

(Continued)

FOREIGN PATENT DOCUMENTS

| CA | 2698078 A1 | 3/2010 |
| CN | 112603295 A | 2/2003 |

(Continued)

OTHER PUBLICATIONS

International Searching Authority, Search Report and Written Opinion for International Application No. PCT/US2021/038617, dated Oct. 15, 2021, 12 pages.
(Continued)

*Primary Examiner* — George Manuel
(74) *Attorney, Agent, or Firm* — Dickinson Wright PLLC; Stephen A. Mason; Jonathan H. Harder

(57) ABSTRACT

Systems and methods for identifying a condition of a user. A treatment apparatus is configured to be manipulated by the user for performing an exercise, and an interface is communicably coupled to the treatment apparatus. One or more sensors are configured to sense one or more characteristics of an anatomical structure of the user. A processing device and a memory is communicatively coupled to the processing device. The memory includes computer readable instructions, that when executed by the processing device, cause the processing device to: receive, from the sensors, one or more sensor inputs representative of the one or more of characteristics of the anatomical structures; calculate an infection probability of a disease based on the one or more (Continued)

characteristics of the anatomical structures; and output, to the interface, a representation of the infection probability.

30 Claims, 11 Drawing Sheets

Related U.S. Application Data application No. 17/021,895, filed on Sep. 15, 2020, now Pat. No. 11,071,597.

(60) Provisional application No. 62/910,232, filed on Oct. 3, 2019.

(51) Int. Cl.

| | | |
|---|---|---|
| *G16H 50/30* | (2018.01) | |
| *G16H 50/70* | (2018.01) | |
| *G16H 10/60* | (2018.01) | |
| *G16H 20/10* | (2018.01) | |
| *G16H 40/20* | (2018.01) | |
| *G16H 70/60* | (2018.01) | |
| *A63B 24/00* | (2006.01) | |
| *A61B 5/103* | (2006.01) | |
| *A61B 5/11* | (2006.01) | |
| *A61B 5/01* | (2006.01) | |
| *G16H 40/67* | (2018.01) | |
| *A63B 22/06* | (2006.01) | |

(52) U.S. Cl.
CPC ............ *A61B 5/486* (2013.01); *A61B 5/4824* (2013.01); *A61B 5/4884* (2013.01); *A61B 5/7246* (2013.01); *A61B 5/7275* (2013.01); *A61B 5/7282* (2013.01); *A61B 5/742* (2013.01); *A61B 5/7405* (2013.01); *A61B 5/7455* (2013.01); *A61B 5/7465* (2013.01); *A63B 24/0062* (2013.01); *G16H 10/60* (2018.01); *G16H 20/10* (2018.01); *G16H 40/20* (2018.01); *G16H 40/67* (2018.01); *G16H 50/30* (2018.01); *G16H 50/70* (2018.01); *G16H 70/60* (2018.01); *A61B 5/7267* (2013.01); *A63B 2022/0647* (2013.01)

(58) Field of Classification Search
CPC ..... A61B 5/1118; A61B 5/221; A61B 5/4824; A61B 5/486; A61B 5/4884; A61B 5/7246; A61B 5/7267; A61B 5/7275; A61B 5/7282; A61B 5/7405; A61B 5/742; A61B 5/7455; A61B 5/7465; A61H 1/0214; A61H 1/024; A61H 2201/1215; A61H 2201/1261; A61H 2201/164; A61H 2201/501; A61H 2201/5043; A61H 2201/5061; A61H 2201/5064; A61H 2201/5069; A61H 2201/5071; A61H 2201/5092; A61H 2201/5097; A61H 2203/0431; A61H 2205/10; A63B 2022/0094; A63B 2022/0623; A63B 2022/0647; A63B 2071/0625; A63B 2071/063; A63B 2071/0655; A63B 2071/0675; A63B 2071/068; A63B 2220/10; A63B 2220/17; A63B 2220/20; A63B 2220/30; A63B 2220/51; A63B 2220/52; A63B 2220/80; A63B 2220/806; A63B 2220/807; A63B 2220/808; A63B 2220/833; A63B 2225/09; A63B 2225/093; A63B 2225/20; A63B 2225/50; A63B 2230/50; A63B 22/0605; A63B 22/0694; A63B 24/0062; A63B 71/0622; G16H 10/60; G16H 15/00; G16H 20/10; G16H 20/30; G16H 20/40; G16H 40/20; G16H 40/63; G16H 40/67; G16H 50/20; G16H 50/30; G16H 50/70; G16H 70/60; G16H 80/00
See application file for complete search history.

(56) References Cited

U.S. PATENT DOCUMENTS

| | | |
|---|---|---|
| 446,671 A | 2/1891 | Elliot |
| 610,157 A | 8/1898 | Campbell |
| 631,276 A | 8/1899 | Bulova |
| 823,712 A | 6/1906 | Uhlmann |
| 1,149,029 A | 8/1915 | Clark |
| 1,227,743 A | 5/1917 | Burgedorfp |
| 1,784,230 A | 12/1930 | Freeman |
| 3,081,645 A | 3/1963 | Bergfors |
| 3,100,640 A | 8/1963 | Weitzel |
| 3,137,014 A | 6/1964 | Meucci |
| 3,143,316 A | 8/1964 | Shapiro |
| 3,713,438 A | 1/1973 | Knutsen |
| 3,744,480 A | 7/1973 | Gause et al. |
| 3,888,136 A | 6/1975 | Lapeyre |
| 4,079,957 A | 3/1978 | Blease |
| 4,408,613 A | 10/1983 | Relyea |
| 4,436,097 A | 3/1984 | Cunningham |
| 4,446,753 A | 5/1984 | Nagano |
| 4,477,072 A | 10/1984 | DeCloux |
| 4,499,900 A | 2/1985 | Petrofsky et al. |
| 4,509,742 A | 4/1985 | Cones |
| 4,606,241 A | 8/1986 | Fredriksson |
| 4,611,807 A | 9/1986 | Castillo |
| 4,616,823 A | 10/1986 | Yang |
| 4,648,287 A | 3/1987 | Preskitt |
| 4,673,178 A | 6/1987 | Dwight |
| 4,822,032 A | 4/1989 | Whitmore et al. |
| 4,824,104 A | 4/1989 | Bloch |
| 4,850,245 A | 7/1989 | Feamster et al. |
| 4,858,942 A | 8/1989 | Rodriguez |
| 4,869,497 A | 9/1989 | Stewart et al. |
| 4,915,374 A | 4/1990 | Watkins |
| 4,930,768 A | 6/1990 | Lapcevic |
| 4,932,650 A | 6/1990 | Bingham et al. |
| 4,961,570 A | 10/1990 | Chang |
| 5,137,501 A | 8/1992 | Mertesdorf |
| 5,161,430 A | 11/1992 | Febey |
| 5,202,794 A | 4/1993 | Schnee et al. |
| 5,240,417 A | 8/1993 | Smithson et al. |
| 5,247,853 A | 9/1993 | Dalebout |
| 5,256,117 A | 10/1993 | Potts et al. |
| D342,299 S | 12/1993 | Birrell et al. |
| 5,282,748 A | 2/1994 | Little |
| 5,284,131 A | 2/1994 | Gray |
| 5,316,532 A | 5/1994 | Butler |
| 5,324,241 A | 6/1994 | Artigues et al. |
| 5,336,147 A | 8/1994 | Sweeney, III |
| 5,338,272 A | 8/1994 | Sweeney, III |
| 5,361,649 A | 11/1994 | Slocum, Jr. |
| 5,429,140 A | 7/1995 | Burdea et al. |
| 5,458,022 A | 10/1995 | Mattfeld et al. |
| 5,487,713 A | 1/1996 | Butler |
| 5,566,589 A | 10/1996 | Buck |
| 5,580,338 A | 12/1996 | Scelta et al. |
| 5,676,349 A | 10/1997 | Wilson |
| 5,685,804 A | 11/1997 | Whan-Tong et al. |
| 5,738,636 A | 4/1998 | Saringer et al. |
| 5,860,941 A | 1/1999 | Saringer et al. |
| 5,950,813 A | 9/1999 | Hoskins et al. |
| 6,053,847 A | 4/2000 | Stearns et al. |
| 6,077,201 A | 6/2000 | Cheng |
| 6,102,834 A | 8/2000 | Chen |
| 6,110,130 A | 8/2000 | Kramer |
| 6,155,958 A | 12/2000 | Goldberg |
| 6,182,029 B1 | 1/2001 | Friedman |
| D438,580 S | 3/2001 | Shaw |
| 6,253,638 B1 | 7/2001 | Bermudez |

(56) References Cited

U.S. PATENT DOCUMENTS

| | | |
|---|---|---|
| 6,267,735 B1 | 7/2001 | Blanchard et al. |
| 6,273,863 B1 | 8/2001 | Avni et al. |
| D450,100 S | 11/2001 | Hsu |
| D450,101 S | 11/2001 | Hsu |
| D451,972 S | 12/2001 | Easley |
| D452,285 S | 12/2001 | Easley |
| D454,605 S | 3/2002 | Lee |
| 6,371,891 B1 | 4/2002 | Speas |
| D459,776 S | 7/2002 | Lee |
| 6,413,190 B1 | 7/2002 | Wood et al. |
| 6,430,436 B1 | 8/2002 | Richter |
| 6,436,058 B1 | 8/2002 | Krahner et al. |
| 6,474,193 B1 | 11/2002 | Farney |
| 6,491,649 B1 | 12/2002 | Ombrellaro |
| 6,535,861 B1 | 3/2003 | OConnor et al. |
| 6,543,309 B2 | 4/2003 | Heim |
| 6,589,139 B1 | 7/2003 | Butterworth |
| 6,602,191 B2 | 8/2003 | Quy |
| 6,626,805 B1 | 9/2003 | Lightbody |
| 6,640,662 B1 | 11/2003 | Baxter |
| 6,652,425 B1 | 11/2003 | Martin et al. |
| 6,820,517 B1 | 11/2004 | Farney |
| 6,865,969 B2 | 3/2005 | Stevens |
| 6,890,312 B1 | 5/2005 | Priester et al. |
| 6,895,834 B1 | 5/2005 | Baalz |
| 7,156,665 B1 | 1/2007 | OConnor et al. |
| 7,169,085 B1 | 1/2007 | Killin et al. |
| 7,204,788 B2 | 4/2007 | Andrews |
| 7,209,886 B2 | 4/2007 | Kimmel |
| 7,226,394 B2 | 6/2007 | Johnson |
| RE39,904 E | 10/2007 | Lee |
| 7,507,188 B2 | 3/2009 | Nurre |
| 7,594,879 B2 | 9/2009 | Johnson |
| 7,778,851 B2 | 8/2010 | Schoenberg et al. |
| 7,809,601 B2 | 10/2010 | Shaya et al. |
| 7,833,135 B2 | 11/2010 | Radow et al. |
| 7,837,472 B1 | 11/2010 | Elsmore et al. |
| 7,955,219 B2 | 6/2011 | Birrell et al. |
| 7,974,689 B2 | 7/2011 | Volpe et al. |
| 7,988,599 B2 | 8/2011 | Ainsworth et al. |
| 8,079,937 B2 | 12/2011 | Bedell |
| 8,287,434 B2 | 10/2012 | Zavadsky et al. |
| 8,419,593 B2 | 4/2013 | Ainsworth et al. |
| 8,465,398 B2 | 6/2013 | Lee et al. |
| 8,506,458 B2 | 8/2013 | Dugan |
| 8,540,515 B2 | 9/2013 | Williams et al. |
| 8,540,516 B2 | 9/2013 | Williams et al. |
| 8,556,778 B1 | 10/2013 | Dugan |
| 8,613,689 B2 | 12/2013 | Dyer et al. |
| 8,672,812 B2 | 3/2014 | Dugan |
| 8,751,264 B2 | 6/2014 | Beraja et al. |
| 8,784,273 B2 | 7/2014 | Dugan |
| 8,823,448 B1 | 9/2014 | Shen |
| 8,979,711 B2 | 3/2015 | Dugan |
| 9,167,281 B2 | 10/2015 | Petrov et al. |
| D744,050 S | 11/2015 | Colburn |
| 9,248,071 B1 | 2/2016 | Brenda |
| 9,272,185 B2 | 3/2016 | Dugan |
| 9,283,434 B1 | 3/2016 | Wu |
| 9,311,789 B1 | 4/2016 | Gwin |
| 9,367,668 B2 | 6/2016 | Flynt et al. |
| 9,409,054 B2 | 8/2016 | Dugan |
| 9,443,205 B2 | 9/2016 | Wall |
| 9,480,873 B2 | 11/2016 | Chuang |
| 9,481,428 B2 | 11/2016 | Gros |
| 9,566,472 B2 | 2/2017 | Dugan |
| 9,579,056 B2 | 2/2017 | Rosenbek et al. |
| 9,629,558 B2 | 4/2017 | Yuen et al. |
| D794,142 S | 8/2017 | Zhou |
| 9,717,947 B2 | 8/2017 | Lin |
| 9,737,761 B1 | 8/2017 | Govindarajan |
| 9,782,621 B2 | 10/2017 | Chiang et al. |
| 9,872,087 B2 | 1/2018 | DelloStritto et al. |
| 9,872,637 B2 | 1/2018 | Kording et al. |
| 9,914,053 B2 | 3/2018 | Dugan |
| 9,919,198 B2 | 3/2018 | Romeo et al. |
| 9,937,382 B2 | 4/2018 | Dugan |
| 9,939,784 B1 | 4/2018 | Berardinelli |
| 10,074,148 B2 | 9/2018 | Cashman et al. |
| 10,130,298 B2 | 11/2018 | Mokaya et al. |
| 10,155,134 B2 | 12/2018 | Dugan |
| 10,159,872 B2 | 12/2018 | Sasaki et al. |
| 10,173,094 B2 | 1/2019 | Gomberg |
| 10,173,095 B2 | 1/2019 | Gomberg et al. |
| 10,173,096 B2 | 1/2019 | Gomberg et al. |
| 10,173,097 B2 | 1/2019 | Gomberg et al. |
| 10,226,663 B2 | 3/2019 | Gomberg et al. |
| 10,325,070 B2 | 6/2019 | Beale et al. |
| 10,327,697 B1 | 6/2019 | Stein et al. |
| 10,424,033 B2 | 9/2019 | Romeo |
| 10,430,552 B2 | 10/2019 | Mihai |
| 10,542,914 B2 | 1/2020 | Forth et al. |
| 10,546,467 B1 | 1/2020 | Luciano, Jr. et al. |
| 10,569,122 B2 | 2/2020 | Johnson |
| 10,572,626 B2 | 2/2020 | Balram |
| 10,576,331 B2 | 3/2020 | Kuo |
| 10,625,114 B2 | 4/2020 | Ercanbrack |
| 10,646,746 B1 | 5/2020 | Gomberg et al. |
| 10,660,534 B2 | 5/2020 | Lee et al. |
| 10,678,890 B2 | 6/2020 | Bitran et al. |
| 10,685,092 B2 | 6/2020 | Paparella et al. |
| 10,777,200 B2 | 9/2020 | Will et al. |
| 10,792,495 B2 | 10/2020 | Izvorski et al. |
| 10,874,905 B2 | 12/2020 | Belson et al. |
| D907,143 S | 1/2021 | Ach et al. |
| 10,918,332 B2 | 2/2021 | Belson et al. |
| 10,931,643 B1 | 2/2021 | Neumann |
| 11,000,735 B2 | 5/2021 | Orady et al. |
| 11,045,709 B2 | 6/2021 | Putnam |
| 11,065,527 B2 | 7/2021 | Putnam |
| 11,069,436 B2 | 7/2021 | Mason et al. |
| 11,071,597 B2 | 7/2021 | Posnack et al. |
| 11,075,000 B2 | 7/2021 | Mason et al. |
| D928,635 S | 8/2021 | Hacking et al. |
| 11,087,865 B2 | 8/2021 | Mason et al. |
| 11,101,028 B2 | 8/2021 | Mason et al. |
| 11,107,591 B1 | 8/2021 | Mason |
| 11,139,060 B2 | 10/2021 | Mason et al. |
| 11,185,735 B2 | 11/2021 | Arn et al. |
| D939,644 S | 12/2021 | Ach et al. |
| D940,797 S | 1/2022 | Ach et al. |
| 11,229,727 B2 | 1/2022 | Tatonetti |
| 11,272,879 B2 | 3/2022 | Wiedenhoefer et al. |
| 11,282,599 B2 | 3/2022 | Mason et al. |
| 11,282,604 B2 | 3/2022 | Mason et al. |
| 11,282,608 B2 | 3/2022 | Mason et al. |
| 11,284,797 B2 | 3/2022 | Mason et al. |
| D948,639 S | 4/2022 | Ach et al. |
| 11,295,848 B2 | 4/2022 | Mason et al. |
| 11,309,085 B2 | 4/2022 | Mason et al. |
| 11,317,975 B2 | 5/2022 | Mason et al. |
| 11,325,005 B2 | 5/2022 | Mason et al. |
| 11,328,807 B2 | 5/2022 | Mason et al. |
| 11,337,648 B2 | 5/2022 | Mason |
| 11,348,683 B2 | 5/2022 | Guaneri et al. |
| 11,404,150 B2 | 8/2022 | Guaneri et al. |
| 11,410,768 B2 | 8/2022 | Mason et al. |
| 2002/0072452 A1 | 6/2002 | Torkelson |
| 2002/0160883 A1 | 10/2002 | Dugan |
| 2003/0036683 A1 | 2/2003 | Kehr et al. |
| 2003/0064863 A1 | 4/2003 | Chen |
| 2003/0092536 A1 | 5/2003 | Romanelli et al. |
| 2003/0109814 A1 | 6/2003 | Rummerfield |
| 2003/0181832 A1 | 9/2003 | Carnahan et al. |
| 2004/0102931 A1 | 5/2004 | Ellis et al. |
| 2004/0106502 A1 | 6/2004 | Sher |
| 2004/0147969 A1 | 7/2004 | Mann et al. |
| 2004/0172093 A1 | 9/2004 | Rummerfield |
| 2004/0194572 A1 | 10/2004 | Kim |
| 2005/0020411 A1 | 1/2005 | Andrews |
| 2005/0043153 A1 | 2/2005 | Krietzman |
| 2005/0049122 A1 | 3/2005 | Vallone et al. |
| 2005/0085346 A1 | 4/2005 | Johnson |
| 2005/0085353 A1 | 4/2005 | Johnson |

(56) References Cited

U.S. PATENT DOCUMENTS

| | | |
|---|---|---|
| 2005/0274220 A1 | 12/2005 | Reboullet |
| 2006/0003871 A1 | 1/2006 | Houghton |
| 2006/0064329 A1 | 3/2006 | Abolfathi et al. |
| 2006/0247095 A1 | 11/2006 | Rummerfield |
| 2007/0042868 A1 | 2/2007 | Fisher et al. |
| 2007/0137307 A1 | 6/2007 | Gruben et al. |
| 2007/0173392 A1 | 7/2007 | Stanford |
| 2007/0287597 A1 | 12/2007 | Cameron |
| 2008/0021834 A1 | 1/2008 | Holla et al. |
| 2008/0153592 A1 | 6/2008 | James-Herbert |
| 2008/0161166 A1 | 7/2008 | Lo |
| 2008/0300914 A1 | 12/2008 | Karkanias et al. |
| 2009/0011907 A1 | 1/2009 | Radow et al. |
| 2009/0058635 A1 | 3/2009 | LaLonde et al. |
| 2009/0070138 A1 | 3/2009 | Langheier et al. |
| 2009/0211395 A1 | 8/2009 | Mul'e |
| 2009/0270227 A1 | 10/2009 | Ashby et al. |
| 2010/0048358 A1 | 2/2010 | Tchao et al. |
| 2010/0121160 A1 | 5/2010 | Stark et al. |
| 2010/0173747 A1 | 7/2010 | Chen et al. |
| 2010/0248899 A1 | 9/2010 | Bedell et al. |
| 2010/0248905 A1 | 9/2010 | Lu |
| 2010/0268304 A1 | 10/2010 | Matos |
| 2010/0298102 A1 | 11/2010 | Bosecker et al. |
| 2011/0047108 A1 | 2/2011 | Chakrabarty et al. |
| 2011/0172059 A1 | 7/2011 | Watterson et al. |
| 2011/0218814 A1 | 9/2011 | Coats |
| 2011/0275483 A1 | 11/2011 | Dugan |
| 2012/0065987 A1 | 3/2012 | Farooq et al. |
| 2012/0116258 A1 | 5/2012 | Lee |
| 2012/0167709 A1 | 7/2012 | Chen et al. |
| 2012/0183939 A1 | 7/2012 | Aragones et al. |
| 2012/0190502 A1 | 7/2012 | Paulus et al. |
| 2012/0295240 A1 | 11/2012 | Walker et al. |
| 2012/0310667 A1 | 12/2012 | Altman et al. |
| 2013/0123071 A1 | 5/2013 | Rhea |
| 2013/0123667 A1 | 5/2013 | Komatireddy et al. |
| 2013/0137550 A1 | 5/2013 | Skinner et al. |
| 2013/0178334 A1 | 7/2013 | Brammer |
| 2013/0296987 A1 | 11/2013 | Rogers et al. |
| 2013/0318027 A1* | 11/2013 | Almogy .............. G16H 50/20 706/52 |
| 2014/0006042 A1 | 1/2014 | Keefe et al. |
| 2014/0011640 A1 | 1/2014 | Dugan |
| 2014/0113768 A1 | 4/2014 | Lin et al. |
| 2014/0155129 A1 | 6/2014 | Dugan |
| 2014/0172460 A1 | 6/2014 | Kohli |
| 2014/0188009 A1 | 7/2014 | Lange et al. |
| 2014/0194250 A1 | 7/2014 | Reich et al. |
| 2014/0194251 A1 | 7/2014 | Reich et al. |
| 2014/0207264 A1 | 7/2014 | Quy |
| 2014/0207486 A1 | 7/2014 | Carty et al. |
| 2014/0246499 A1 | 9/2014 | Proud et al. |
| 2014/0256511 A1 | 9/2014 | Smith |
| 2014/0257837 A1 | 9/2014 | Walker et al. |
| 2014/0274565 A1 | 9/2014 | Boyette et al. |
| 2014/0274622 A1 | 9/2014 | Leonhard |
| 2014/0309083 A1 | 10/2014 | Dugan |
| 2014/0315689 A1 | 10/2014 | Vauquelin et al. |
| 2014/0322686 A1 | 10/2014 | Kang |
| 2015/0045700 A1 | 2/2015 | Cavanagh et al. |
| 2015/0088544 A1 | 3/2015 | Goldberg |
| 2015/0151162 A1 | 6/2015 | Dugan |
| 2015/0158549 A1 | 6/2015 | Gros et al. |
| 2015/0161331 A1 | 6/2015 | Oleynik |
| 2015/0290061 A1 | 10/2015 | Stafford et al. |
| 2015/0339442 A1 | 11/2015 | Oleynik |
| 2015/0341812 A1 | 11/2015 | Dion et al. |
| 2015/0379232 A1 | 12/2015 | Mainwaring et al. |
| 2016/0007885 A1 | 1/2016 | Basta |
| 2016/0023081 A1 | 1/2016 | Popa-Simil |
| 2016/0117471 A1 | 4/2016 | Belt et al. |
| 2016/0140319 A1 | 5/2016 | Stark et al. |
| 2016/0151670 A1 | 6/2016 | Dugan |
| 2016/0166881 A1 | 6/2016 | Ridgel et al. |
| 2016/0275259 A1 | 9/2016 | Nolan et al. |
| 2016/0302721 A1 | 10/2016 | Wiedenhoefer et al. |
| 2016/0317869 A1 | 11/2016 | Dugan |
| 2016/0322078 A1 | 11/2016 | Bose et al. |
| 2016/0325140 A1 | 11/2016 | Wu |
| 2016/0332028 A1 | 11/2016 | Melnik |
| 2017/0004260 A1 | 1/2017 | Moturu et al. |
| 2017/0033375 A1 | 2/2017 | Ohmori et al. |
| 2017/0042467 A1 | 2/2017 | Herr et al. |
| 2017/0046488 A1 | 2/2017 | Pereira |
| 2017/0065851 A1 | 3/2017 | Deluca et al. |
| 2017/0080320 A1 | 3/2017 | Smith |
| 2017/0095670 A1 | 4/2017 | Ghaffar et al. |
| 2017/0095692 A1 | 4/2017 | Chang et al. |
| 2017/0095693 A1 | 4/2017 | Chang et al. |
| 2017/0106242 A1 | 4/2017 | Dugan |
| 2017/0113092 A1 | 4/2017 | Johnson |
| 2017/0128769 A1 | 5/2017 | Long et al. |
| 2017/0132947 A1 | 5/2017 | Maeda et al. |
| 2017/0136296 A1 | 5/2017 | Barrera et al. |
| 2017/0143261 A1 | 5/2017 | Wiedenhoefer et al. |
| 2017/0147789 A1 | 5/2017 | Wiedenhoefer et al. |
| 2017/0168555 A1 | 6/2017 | Munoz et al. |
| 2017/0181698 A1 | 6/2017 | Wiedenhoefer et al. |
| 2017/0190052 A1 | 7/2017 | Jaekel et al. |
| 2017/0209766 A1 | 7/2017 | Riley et al. |
| 2017/0243028 A1 | 8/2017 | LaFever et al. |
| 2017/0266501 A1 | 9/2017 | Sanders et al. |
| 2017/0278209 A1 | 9/2017 | Olsen et al. |
| 2017/0282015 A1 | 10/2017 | Wicks et al. |
| 2017/0300654 A1 | 10/2017 | Stein et al. |
| 2017/0312614 A1 | 11/2017 | Tran et al. |
| 2017/0329917 A1 | 11/2017 | McRaith et al. |
| 2017/0333755 A1 | 11/2017 | Rider |
| 2017/0337033 A1 | 11/2017 | Duyan et al. |
| 2017/0337334 A1 | 11/2017 | Stanczak |
| 2017/0344726 A1 | 11/2017 | Duffy et al. |
| 2017/0360586 A1 | 12/2017 | Dempers et al. |
| 2017/0368413 A1 | 12/2017 | Shavit |
| 2018/0017806 A1 | 1/2018 | Wang et al. |
| 2018/0052962 A1 | 2/2018 | Van Der Koijk et al. |
| 2018/0056104 A1 | 3/2018 | Cromie et al. |
| 2018/0071565 A1 | 3/2018 | Gomberg et al. |
| 2018/0071566 A1 | 3/2018 | Gomberg et al. |
| 2018/0071569 A1 | 3/2018 | Gomberg et al. |
| 2018/0071570 A1 | 3/2018 | Gomberg et al. |
| 2018/0071571 A1 | 3/2018 | Gomberg et al. |
| 2018/0071572 A1 | 3/2018 | Gomberg et al. |
| 2018/0075205 A1 | 3/2018 | Moturu et al. |
| 2018/0078843 A1 | 3/2018 | Tran et al. |
| 2018/0085615 A1 | 3/2018 | Astolfi et al. |
| 2018/0102190 A1 | 4/2018 | Hogue et al. |
| 2018/0178061 A1 | 6/2018 | O'larte et al. |
| 2018/0199855 A1* | 7/2018 | Odame .............. A61B 5/6822 |
| 2018/0200577 A1 | 7/2018 | Dugan |
| 2018/0220935 A1 | 8/2018 | Tadano et al. |
| 2018/0228682 A1 | 8/2018 | Bayerlein et al. |
| 2018/0240552 A1 | 8/2018 | Tuyl et al. |
| 2018/0253991 A1 | 9/2018 | Tang et al. |
| 2018/0256079 A1 | 9/2018 | Yang et al. |
| 2018/0263530 A1 | 9/2018 | Jung |
| 2018/0271432 A1 | 9/2018 | Auchinleck et al. |
| 2018/0272184 A1 | 9/2018 | Vassilaros et al. |
| 2018/0280784 A1 | 10/2018 | Romeo et al. |
| 2018/0296157 A1 | 10/2018 | Bleich et al. |
| 2018/0330058 A1 | 11/2018 | Bates |
| 2018/0330824 A1 | 11/2018 | Athey et al. |
| 2018/0360340 A1 | 12/2018 | Rehse et al. |
| 2018/0373844 A1 | 12/2018 | Ferrandez-Escamez et al. |
| 2019/0019578 A1 | 1/2019 | Vaccaro |
| 2019/0030415 A1 | 1/2019 | Volpe, Jr. |
| 2019/0031284 A1 | 1/2019 | Fuchs |
| 2019/0060708 A1 | 2/2019 | Fung |
| 2019/0065970 A1 | 2/2019 | Bonutti et al. |
| 2019/0066832 A1 | 2/2019 | Kang et al. |
| 2019/0076701 A1 | 3/2019 | Dugan |
| 2019/0088356 A1 | 3/2019 | Oliver et al. |
| 2019/0111299 A1 | 4/2019 | Radcliffe et al. |
| 2019/0115097 A1 | 4/2019 | Macoviak et al. |

(56) References Cited

U.S. PATENT DOCUMENTS

| | | |
|---|---|---|
| 2019/0117128 A1 | 4/2019 | Chen et al. |
| 2019/0126099 A1 | 5/2019 | Hoang |
| 2019/0132948 A1 | 5/2019 | Longinotti-Buitoni et al. |
| 2019/0134454 A1 | 5/2019 | Mahoney et al. |
| 2019/0137988 A1 | 5/2019 | Celia et al. |
| 2019/0167988 A1 | 6/2019 | Shahriari et al. |
| 2019/0172587 A1 | 6/2019 | Park et al. |
| 2019/0175988 A1 | 6/2019 | Volterrani et al. |
| 2019/0200920 A1 | 7/2019 | Tien et al. |
| 2019/0209891 A1 | 7/2019 | Fung |
| 2019/0240103 A1 | 8/2019 | Hepler et al. |
| 2019/0240541 A1 | 8/2019 | Denton et al. |
| 2019/0244540 A1 | 8/2019 | Errante et al. |
| 2019/0269343 A1 | 9/2019 | Ramos Murguialday et al. |
| 2019/0274523 A1 | 9/2019 | Bates et al. |
| 2019/0290964 A1 | 9/2019 | Oren |
| 2019/0304584 A1 | 10/2019 | Savolainen |
| 2019/0307983 A1 | 10/2019 | Goldman |
| 2019/0354632 A1 | 11/2019 | Mital et al. |
| 2019/0366146 A1 | 12/2019 | Tong et al. |
| 2019/0388728 A1 | 12/2019 | Wang et al. |
| 2020/0005928 A1 | 1/2020 | Daniel |
| 2020/0051446 A1 | 2/2020 | Rubinstein et al. |
| 2020/0066390 A1 | 2/2020 | Svendrys et al. |
| 2020/0085300 A1 | 3/2020 | Kwatra et al. |
| 2020/0093418 A1 | 3/2020 | Kluger et al. |
| 2020/0143922 A1 | 5/2020 | Chekroud et al. |
| 2020/0151595 A1 | 5/2020 | Jayalath et al. |
| 2020/0151646 A1 | 5/2020 | De La Fuente Sanchez |
| 2020/0152339 A1 | 5/2020 | Pulitzer et al. |
| 2020/0160198 A1 | 5/2020 | Reeves et al. |
| 2020/0170876 A1 | 6/2020 | Kapure et al. |
| 2020/0176098 A1 | 6/2020 | Lucas et al. |
| 2020/0197744 A1 | 6/2020 | Schweighofer |
| 2020/0221975 A1 | 7/2020 | Basta et al. |
| 2020/0267487 A1 | 8/2020 | Siva |
| 2020/0275886 A1 | 9/2020 | Mason |
| 2020/0289045 A1 | 9/2020 | Hacking et al. |
| 2020/0289046 A1 | 9/2020 | Hacking et al. |
| 2020/0289879 A1 | 9/2020 | Hacking et al. |
| 2020/0289880 A1 | 9/2020 | Hacking et al. |
| 2020/0289881 A1 | 9/2020 | Hacking et al. |
| 2020/0289889 A1 | 9/2020 | Hacking et al. |
| 2020/0293712 A1 | 9/2020 | Potts et al. |
| 2020/0334972 A1 | 10/2020 | Gopalakrishnan |
| 2020/0357299 A1 | 11/2020 | Patel et al. |
| 2020/0395112 A1 | 12/2020 | Ronner |
| 2020/0401224 A1 | 12/2020 | Cotton |
| 2021/0074178 A1 | 3/2021 | Ilan et al. |
| 2021/0076981 A1 | 3/2021 | Hacking et al. |
| 2021/0077860 A1 | 3/2021 | Posnack et al. |
| 2021/0098129 A1 | 4/2021 | Neumann |
| 2021/0101051 A1 | 4/2021 | Posnack et al. |
| 2021/0113890 A1 | 4/2021 | Posnack et al. |
| 2021/0127974 A1 | 5/2021 | Mason et al. |
| 2021/0128080 A1 | 5/2021 | Mason et al. |
| 2021/0128255 A1 | 5/2021 | Mason et al. |
| 2021/0128978 A1 | 5/2021 | Gilstrom et al. |
| 2021/0134412 A1 | 5/2021 | Guaneri et al. |
| 2021/0134425 A1 | 5/2021 | Mason et al. |
| 2021/0134428 A1 | 5/2021 | Mason et al. |
| 2021/0134430 A1 | 5/2021 | Mason et al. |
| 2021/0134432 A1 | 5/2021 | Mason et al. |
| 2021/0134456 A1 | 5/2021 | Posnack et al. |
| 2021/0134457 A1 | 5/2021 | Mason et al. |
| 2021/0134458 A1 | 5/2021 | Mason et al. |
| 2021/0134463 A1 | 5/2021 | Mason et al. |
| 2021/0138304 A1 | 5/2021 | Mason et al. |
| 2021/0142875 A1 | 5/2021 | Mason et al. |
| 2021/0142893 A1 | 5/2021 | Guaneri et al. |
| 2021/0142898 A1 | 5/2021 | Mason et al. |
| 2021/0142903 A1 | 5/2021 | Mason et al. |
| 2021/0144074 A1 | 5/2021 | Guaneri et al. |
| 2021/0186419 A1 | 6/2021 | Van Ee et al. |
| 2021/0202090 A1 | 7/2021 | ODonovan et al. |
| 2021/0202103 A1 | 7/2021 | Bostic et al. |
| 2021/0244998 A1 | 8/2021 | Hacking et al. |
| 2021/0345879 A1 | 11/2021 | Mason et al. |
| 2021/0345975 A1 | 11/2021 | Mason et al. |
| 2021/0350888 A1 | 11/2021 | Guaneri et al. |
| 2021/0350898 A1 | 11/2021 | Mason et al. |
| 2021/0350899 A1 | 11/2021 | Mason et al. |
| 2021/0350901 A1 | 11/2021 | Mason et al. |
| 2021/0350902 A1 | 11/2021 | Mason et al. |
| 2021/0350914 A1 | 11/2021 | Guaneri et al. |
| 2021/0350926 A1 | 11/2021 | Mason et al. |
| 2021/0366587 A1 | 11/2021 | Mason et al. |
| 2021/0383909 A1 | 12/2021 | Mason et al. |
| 2021/0391091 A1 | 12/2021 | Mason |
| 2021/0407670 A1 | 12/2021 | Mason et al. |
| 2022/0015838 A1 | 1/2022 | Posnack et al. |
| 2022/0047921 A1 | 2/2022 | Bissonnette et al. |
| 2022/0079690 A1 | 3/2022 | Mason et al. |
| 2022/0080256 A1 | 3/2022 | Arn et al. |
| 2022/0105384 A1 | 4/2022 | Hacking et al. |
| 2022/0105385 A1 | 4/2022 | Hacking et al. |
| 2022/0115133 A1 | 4/2022 | Mason et al. |
| 2022/0126169 A1 | 4/2022 | Mason |
| 2022/0148725 A1 | 5/2022 | Mason et al. |
| 2022/0158916 A1 | 5/2022 | Mason et al. |
| 2022/0193491 A1 | 6/2022 | Mason et al. |
| 2022/0230729 A1 | 7/2022 | Mason et al. |
| 2022/0238223 A1 | 7/2022 | Mason et al. |
| 2022/0262483 A1 | 8/2022 | Rosenberg et al. |
| 2022/0266094 A1 | 8/2022 | Mason et al. |
| 2022/0270738 A1 | 8/2022 | Mason et al. |
| 2022/0273986 A1 | 9/2022 | Mason |
| 2022/0288460 A1 | 9/2022 | Mason |
| 2022/0288461 A1 | 9/2022 | Ashley et al. |
| 2022/0288462 A1 | 9/2022 | Ashley et al. |
| 2022/0293257 A1 | 9/2022 | Guaneri et al. |

FOREIGN PATENT DOCUMENTS

| | | |
|---|---|---|
| CN | 202220794 U | 5/2012 |
| CN | 103488880 A | 1/2014 |
| CN | 104335211 A | 2/2015 |
| CN | 105620643 A | 6/2016 |
| CN | 105683977 A | 6/2016 |
| CN | 105894088 A | 8/2016 |
| CN | 105930668 A | 9/2016 |
| CN | 106127646 A | 11/2016 |
| CN | 106510985 A | 3/2017 |
| CN | 107066819 A | 8/2017 |
| CN | 107430641 A | 12/2017 |
| CN | 107736982 A | 2/2018 |
| CN | 207220817 U | 4/2018 |
| CN | 108078737 A | 5/2018 |
| CN | 208573971 U | 3/2019 |
| CN | 110148472 A | 8/2019 |
| CN | 110215188 A | 9/2019 |
| CN | 111105859 A | 5/2020 |
| CN | 111370088 A | 7/2020 |
| CN | 112603295 A | 4/2021 |
| DE | 95019 C | 1/1897 |
| DE | 7628633 U1 | 12/1977 |
| DE | 8519150 U1 | 10/1985 |
| DE | 3732905 A1 | 7/1988 |
| DE | 19619820 C2 | 12/1996 |
| DE | 29620008 U1 | 2/1997 |
| DE | 19947926 A3 | 4/2001 |
| DE | 102018202497 A1 | 8/2018 |
| DE | 102018211212 A1 | 1/2019 |
| DE | 102019108425 B3 | 8/2020 |
| EP | 199600 A2 | 10/1986 |
| EP | 634319 B1 | 10/1999 |
| EP | 1034817 A1 | 9/2000 |
| EP | 2564904 A1 | 3/2013 |
| EP | 3264303 A1 | 1/2018 |
| EP | 3323473 A1 | 5/2018 |
| EP | 3688537 A1 | 8/2020 |
| EP | 3731733 A1 | 11/2020 |
| FR | 2527541 A2 | 12/1983 |
| GB | 141664 A | 11/1920 |

(56) References Cited

FOREIGN PATENT DOCUMENTS

| | | |
|---|---|---|
| GB | 2336140 A | 10/1999 |
| GB | 2372459 A | 8/2002 |
| JP | 2003225875 A | 8/2003 |
| JP | 2013515995 A | 5/2013 |
| JP | 3198173 U | 6/2015 |
| JP | 6659831 B2 | 10/2017 |
| JP | 2019134909 A | 8/2019 |
| JP | 6573739 B1 | 9/2019 |
| JP | 6710357 B1 | 6/2020 |
| JP | 6775757 B1 | 10/2020 |
| JP | 2021026768 A | 2/2021 |
| JP | 2021027917 A | 2/2021 |
| KR | 20020009724 A | 2/2002 |
| KR | 20020065253 A | 8/2002 |
| KR | 20110099953 A | 9/2011 |
| KR | 20150017693 A | 2/2015 |
| KR | 20160093990 A | 8/2016 |
| KR | 20170038837 A | 4/2017 |
| KR | 20190011885 A | 2/2019 |
| KR | 20190056116 A | 5/2019 |
| KR | 101988167 B1 | 6/2019 |
| KR | 102116664 B1 | 7/2019 |
| KR | 102116968 B1 | 3/2020 |
| KR | 20200025290 A | 3/2020 |
| KR | 102162522 B1 | 4/2020 |
| KR | 102142713 B1 | 5/2020 |
| KR | 20200056233 A | 5/2020 |
| KR | 102120828 B1 | 6/2020 |
| KR | 102173553 B1 | 11/2020 |
| KR | 102180079 B1 | 11/2020 |
| KR | 102224618 B1 | 11/2020 |
| KR | 102188766 B1 | 12/2020 |
| KR | 102196793 B1 | 12/2020 |
| KR | 20210006212 A | 1/2021 |
| KR | 102224188 B1 | 3/2021 |
| KR | 102264498 B1 | 6/2021 |
| TW | 442956 B | 7/2014 |
| WO | 1998009687 A | 3/1998 |
| WO | 0149235 A2 | 7/2001 |
| WO | 0151083 A2 | 7/2001 |
| WO | 2001050387 A1 | 7/2001 |
| WO | 2003043494 A1 | 5/2003 |
| WO | 2005018453 A1 | 3/2005 |
| WO | 2006004430 A2 | 1/2006 |
| WO | 2006012694 A1 | 2/2006 |
| WO | 2008114291 A1 | 9/2008 |
| WO | 2014178077 A2 | 11/2014 |
| WO | 2016154318 A1 | 9/2016 |
| WO | 2018171853 A1 | 9/2018 |
| WO | 2019022706 A1 | 1/2019 |
| WO | 2019204876 A1 | 4/2019 |
| WO | 2019083450 A1 | 5/2019 |
| WO | 2020185769 A1 | 3/2020 |
| WO | 2020075190 A1 | 4/2020 |
| WO | 2020130979 A1 | 6/2020 |
| WO | 2020149815 A2 | 7/2020 |
| WO | 2020245727 A1 | 12/2020 |
| WO | 2020249855 A1 | 12/2020 |
| WO | 2020252599 A1 | 12/2020 |
| WO | 2020256577 A1 | 12/2020 |
| WO | 2021021447 A1 | 2/2021 |
| WO | 2021038980 A1 | 3/2021 |
| WO | 2021055427 A1 | 3/2021 |
| WO | 2021055491 A1 | 3/2021 |
| WO | 2021061061 A1 | 4/2021 |
| WO | 2021081094 A1 | 4/2021 |
| WO | 2021138620 A1 | 7/2021 |
| WO | 2021216881 A1 | 10/2021 |
| WO | 2021236542 A1 | 11/2021 |
| WO | 2021236961 A1 | 11/2021 |
| WO | 2021262809 A1 | 12/2021 |

OTHER PUBLICATIONS

International Searching Authority, Search Report and Written Opinion for International Application No. PCT/US20/51008, dated Dec. 10, 2020; 8 pages.
Claris Healthcare Inc.; Claris Reflex Patient Rehabilitation System Brochure, https://clarisreflex.com/, retrieved from internet on Oct. 2, 2019; 5 pages.
International Searching Authority, Search Report and Written Opinion for PCT/US2020/021876, dated May 28, 2020; 7 pages.
FYSIOMED, "16983—Vario adjustable pedal arms", <https://www.fysiomed.com/en/products/16983-vario-adjustable-pedal-arms>, pulled from webpage on Aug. 4, 2020; 1 page.
Matrix, "R3xm Recumbent Cycle", <https://www.matrixfitness.com/en/cardio/cycles/r3xm-recumbent>, pulled from webpage on Aug. 4, 2020; 1 page.
Stephen R. Crow, Authorized Officer, PCT Notification of Transmittal of International Preliminary Report on Patentability, dated Dec. 11, 2018, PCT/US2017/50895, Alexandria, Virginia USA; 52 pages.
PCT International Search Report and Written Opinion, PCT/US17/50895 dated Jan. 12, 2018; 18 pages.
"ROMTech The Modem Techology of Rehabilitation" [retrieved Aug. 19, 2021]. Retrieved from the Internet: <https://https://www.romtech.com>.
HCI Fitness physio trainer, announced 2017 [online], [site visited Nov. 10, 2020], Available from internet, URL: https://www.amazon.com/HCI-Fitness-Physio Trainer-Electronically-Controlled/dp/B0759YMW78/ (Year: 2017).
"HCI Fitness physio trainer, announced 2009 [online], [site visited Nov. 10, 2020], Available from internet, URL: https://vww.amazon.com/HCI-Fitness-PhysioTrainer-Upper-Ergonometer/dp/B001P5GUGM (Year: 2009)".
International Searching Authority, Search Report and Written Opinion for PCT/US20/56661, dated Feb. 12, 2021; 11 pages.
Dor-Haim, "A Novel Digital Platform for a Monitored Home-based Cardiac Rehabilitation Program". Journal of Visualized Experiments. Webpage <https://www.jove.com/video/59019>. Apr. 19, 2019; Entire Document.; 30 pages.
Kobsar, et al., 2018, "Wearable Sensor Data to Track Subject-Specific Movement Patterns Related to Clinical Dutcomes Using a Machine Learning Approach"; 12 pages.
International Search Report and Written Opinion for International Application No. PCT/US2021/032807, dated Sep. 6, 2021, 11 pages.
Jennifer Bresnick, "What is the Role of Natural Language Processing in Healthcare?", pp. 1-7, published Aug. 18, 2016, retrieved on Feb. 1, 2022 from https://healthitanalytics.com/featu res/what-is-the-role-of-natural-language-processing-in-healthcare.
Alex Bellec, "Part-of-Speech tagging tutorial with the Keras Deep Learning library," pp. 1-16, published Mar. 27, 2018, retrieved on Feb. 1, 2022 from https://becominghuman.ai/part-of-speech-tagging-tutorial-with-the-keras-deep-learning-library-d7f93fa05537.
Kavita Ganesan, All you need to know about text preprocessing for NLP and Machine Learning, pp. 1-14, published Feb. 23, 2019, retrieved on Feb. 1, 2022 from https:// towardsdatascience.com/all-you-need-to-know-about-text-preprocessing-for-nlp-and-machine-learning-bcl c5765ff67.
Badreesh Shetty, "Natural Language Processing (NPL) for Machine Learning," pp. 1-13, published Nov. 24, 2018, retrieved on Feb. 1, 2022 from https://towardsdatascience. com/natural-language-processing-nlp-for-machine-learning-d44498845d5b.
Davenport et al., "The Potential For Artificial Intelligence In Healthcare", 2019, Future Healthcare Journal 2019, vol. 6, No. 2: Year: 2019, pp. 1-5.
Ahmed et al., "Artificial Intelligence With Multi-Functional Machine Learning Platform Development For Better Healthcare And Precision Medicine", 2020, Database (Oxford), 2020:baaa010. doi: 10.1093/database/baaa010 (Year 2020), pp. 1-35.
Ruiz Ivan et al., "Towards a physical rehabilitation system using a telemedicine approach", Computer Methods In Biomechanics and Biomedical Engineering: Imaging & Visualization, vol. 8, No. 6, Jul. 28, 2020, pp. 671-680, XP055914810.

(56) References Cited

OTHER PUBLICATIONS

De Canniere Helene et al., "Wearable Monitoring and Interpretable Machine Learning Can Objectively Track Progression in Patients during Cardiac Rehabilitation", Sensors, vol. 20, No. 12, Jun. 26, 2020, XP055914617, pp. 1-15.
Boulanger Pierre et al., "A Low-cost Virtual Reality Bike for Remote Cardiac Rehabilitation", Dec. 7, 2017, Advances in Biometrics: International Conference, ICB 2007, Seoul, Korea, pp. 155-166.
Yin Chieh et al., "A Virtual Reality-Cycling Training System for Lower Limb Balance Improvement", BioMed Research International, vol. 2016, pp. 1-10.
Barrett et al., "Artificial intelligence supported patient self-care in chronic heart failure: a paradigm shift from reactive to predictive, preventive and personalised care," EPMA Journal (2019), pp. 445-464.
Oerkild et al., "Home-based cardiac rehabilitation is an attractive alternative to no cardiac rehabilitation for elderly patients with coronary heart disease: results from a randomised clinical trial," BMJ Open Accessible Medical Research, Nov. 22, 2012, pp. 1-9.
Bravo-Escobar et al., "Effectiveness and safety of a home-based cardiac rehabilitation programme of mixed surveillance in patients with ischemic heart disease at moderate cardiovascular risk: A randomised, controlled clinical trial," BMC Cardiovascular Disorders, 2017, pp. 1-11, vol. 17:66.
Thomas et al., "Home-Based Cardiac Rehabilitation," Circulation, 2019, pp. e69-e89, vol. 140.
Thomas et al., "Home-Based Cardiac Rehabilitation," Journal of the American College of Cardiology, Nov. 1, 2019, pp. 133-153, vol. 74.
Thomas et al., "Home-Based Cardiac Rehabilitation," HHS Public Access, Oct. 2, 2020, pp. 1-39.
Dittus et al., "Exercise-Based Oncology Rehabilitation: Leveraging the Cardiac Rehabilitation Model," Journal of Cardiopulmonary Rehabilitation and Prevention, 2015, pp. 130-139, vol. 35.
Chen et al., "Home-based cardiac rehabilitation improves quality of life, aerobic capacity, and readmission rates in patients with chronic heart failure," Medicine, 2018, pp. 1-5 Vol. 97:4.
Lima de Melo Ghisi et al., "A systematic review of patient education in cardiac patients: Do they increase knowledge and promote health behavior change?," Patient Education and Counseling, 2014, pp. 1-15.
Fang et al., "Use of Outpatient Cardiac Rehabilitation Among Heart Attack Survivors—20 States and the District of Columbia, 2013 and Four States, 2015," Morbidity and Mortality Weekly Report, vol. 66, No. 33, Aug. 25, 2017, pp. 369-873.
Beene et al., "AI and Care Delivery: Emerging Opportunities For Artificial Intelligence To Transform How Care Is Delivered," Nov. 2019, American Hospital Association, pp. 1-12.
Website for "Pedal Exerciser", p. 1, retrieved on Sep. 9, 2022 from https://www.vivehealth.com/collections/physical-therapy-equipment/products/pedalexerciser.
Website for "Functional Knee Brace with ROM", p. 1, retrieved on Sep. 9, 2022 from http://medicalbrace.gr/en/product/functional-knee-brace-with-goniometer-mbtelescopicknee/.
Website for "ComfySplints Goniometer Knee", pp. 1-5, retrieved on Sep. 9, 2022 from https://www.comfysplints.com/product/knee-splints/.
Website for "BMI FlexEze Knee Corrective Orthosis (KCO)", pp. 1-4, retrieved on Sep. 9, 2022 from https://orthobmi.com/products/bmi-flexeze%C2%AE-knee-corrective-orthosis-kco.
Website for "Neoprene Knee Brace with goniometer—Patella ROM MB.4070", pp. 1-4, retrieved on Sep. 9, 2022 from https://www.fortuna.com.gr/en/product/neoprene-knee-brace-with-goniometer-patella-rom-mb-4070/.
Kuiken et al., "Computerized Biofeedback Knee Goniometer: Acceptance and Effect on Exercise Behavior in Post-total Knee Arthroplasty Rehabilitation," Biomedical Engineering Faculty Research and Publications, 2004, pp. 1-10.
Ahmed et al., "Artificial intelligence with multi-functional machine learning platform development for better healthcare and precision medicine," Database, 2020, pp. 1-35.
Davenport et al., "The potential for artificial intelligence in healthcare," Digital Technology, Future Healthcare Journal, 2019, pp. 1-5, vol. 6, No. 2.
Website for "OxeFit XS1", pp. 1-3, retrieved on Sep. 9, 2022 from https://www.oxefit.com/xs1.
Webksite for "Preva Mobile", pp. 1-6, retrieved on Sep. 9, 2022 from https://www.precor.com/en-us/resources/introducing-preva-mobile.
Website for "J-Bike", pp. 1-3, retrieved on Sep. 9, 2022 from https://www.magneticdays.com/en/cycling-for-physical-rehabilitation.
Website for "Excy", pp. 1-12, retrieved on Sep. 9, 2022 from https://excy.com/portable-exercise-rehabilitation-excy-xcs-pro/.
Website for "OxeFit XP1", p. 1, retrieved on Sep. 9, 2022 from https://www.oxefit.com/xp1.

* cited by examiner

SYSTEMS AND METHODS FOR REMOTELY-ENABLED IDENTIFICATION OF A USER INFECTION

CROSS-REFERENCE TO RELATED APPLICATIONS

This application is a continuation of U.S. patent application Ser. No. 17/146,694, filed Jan. 12, 2021, titled "Systems and Methods for Remotely-Enabled Identification of a User Infection," which is a continuation-in-part of U.S. patent application Ser. No. 17/021,895, filed Sep. 15, 2020, titled "Telemedicine for Orthopedic Treatment," which claims priority to and the benefit of U.S. Provisional Patent Application Ser. No. 62/910,232, filed Oct. 3, 2019, titled "Telemedicine for Orthopedic Treatment," the entire disclosures of which are hereby incorporated by reference for all purposes.

BACKGROUND

Subsequent to a procedure (e.g., surgical/invasive procedure to replace a knee or hip), the location of the procedure, or near or distal thereto, may become infected. While some infections may naturally heal without treatment (or without significant treatment), other infections can spread throughout the body, and if left untreated cause, for example, staph or other infections, sepsis (septicaemia), peritonitis, and other life-threatening, life-quality-threatening or other serious medical conditions. For example, a user may be exposed to staphylococcus bacteria during or after a surgical procedure, leading to a staph infection that can spread throughout the users body, i.e., to a location (or locations) other than the location of the procedure. These infections, if left untreated, can cause a range of health issues to the user, from minor skin problems, to amputation of the user's infected limb, to even death in severe cases. Such health issues may occur in temporally, geographically and/or anatomically proximate manners.

To avoid such health issues, some medical professionals schedule routine check-ups, wherein the check-up is based on the type of procedure to the user. In between the routine check-ups, medical professionals may rely on users to detect and "self-diagnose" any health issues resulting from the procedure and to contact them (i.e., the medical professionals) for further diagnosis and/or treatment. In some instances, non-infected users may self-diagnose the health issue incorrectly and schedule unnecessary appointments with their medical professionals, resulting in inefficient uses of medical professional resources.

In some instances, such as during the COVID-19 pandemic, medical professionals may schedule remote medical assistance. Remote medical assistance, also referred to, inter alia, as remote medicine, telemedicine, telemed, telmed, tel-med, or telehealth, is an at least two-way communication between a healthcare provider or providers, such as a physician or a physical therapist, and a patient using audio and/or audiovisual and/or other sensorial or perceptive (e.g., tactile, gustatory, haptic, pressure-sensing-based or electromagnetic (e.g., neurostimulation) communications (e.g., via a computer, a smartphone, or a tablet). Telemedicine may aid a patient in performing various aspects of a rehabilitation regimen for a body part. The patient may use a patient interface in communication with an assistant interface for receiving the remote medical assistance via audio, visual, audiovisual, or other communications described elsewhere herein. Any reference herein to any particular sensorial modality shall be understood to include and to disclose by implication a different one or more sensory modalities.

Telemedicine is an option for healthcare providers to communicate with patients and provide patient care when the patients do not want to or cannot easily go to the healthcare providers' offices. Telemedicine, however, has substantive limitations as the healthcare providers cannot conduct physical examinations of the patients. Rather, the healthcare providers must rely on verbal communication and/or limited remote observation of the patients.

SUMMARY

In general, the present disclosure provides systems and methods for a remotely-enabled identification of a user infection. As used herein, "identification" means both a correct identification of a user infection as well as a medically appropriate, normal-standard-of-care attempt to identify or diagnose the user infection, even if the identification is ultimately incorrect or subject to further refinement or modification by a medical professional.

An aspect of the disclosed embodiments includes a system for identifying characteristics associated with a user infection. The system includes a memory device for storing instructions and a processing device communicatively coupled to the memory device. The processing device is configured to execute the instructions to receive, from one or more sensors, one or more sensor inputs pertaining to a potential infected site or anatomical structure; and to generate, by the processing device, an infection probability associated with the infected site, wherein the infection probability is based on the one or more sensor inputs. Another aspect of the disclosed embodiments includes a system for identifying a condition of a user, such as a user having an infection. The system includes a treatment apparatus configured to be manipulated by the user to perform an exercise, such a peddling a bike-like apparatus. An interface is communicably coupled to the treatment apparatus. One or more sensors are configured to sense one or more characteristics of an anatomical structure of the user. As used herein, an anatomical structure may refer to a structure that is anatomical or to a system that is physiological or to any combination thereof. A processing device and a memory are communicatively coupled to the processing device. The memory includes computer readable instructions that, when executed by the processing device, cause the processing device to: receive, from the sensors, one or more sensor inputs representative of the one or more of characteristics of the anatomical structure; calculate an infection probability of a disease based on the one or more characteristics of the anatomical structure; and output, to the interface, a representation of the infection probability.

Another aspect of the disclosed embodiments includes a system for identifying a condition of a user. A treatment apparatus is configured to be manipulated by the user to perform an exercise, such as peddling a bike-like apparatus. One or more sensors are configured to sense one or more characteristics of an anatomical structure of the user. A processing device and a memory are communicatively coupled to the processing device. The memory includes computer readable instructions that, when executed by the processing device, cause the processing device to: receive, from the sensors, one or more sensor inputs representative of the one or more of characteristics of the anatomical structure; generate, from the one or more characteristics, a baseline characteristic and a disease characteristic; generate an infection probability of a disease, where the probability is based on the one or more characteristics, the baseline characteristic and the disease characteristic.

Another aspect of the disclosed embodiments includes a method for identifying a condition. The method includes a step of receiving, from one or more sensors, one or more sensor inputs representative of one or more of characteristics of the anatomical structure. The method includes the step of calculating an infection probability of a disease based on the one or more characteristics of the anatomical structure. The method also includes the step of outputting, to an interface, a representation of the infection probability.

BRIEF DESCRIPTION OF THE DRAWINGS

For a more complete understanding of this disclosure and its advantages, reference is now made to the following description, taken in conjunction with the accompanying drawings. It is emphasized that, according to common practice, the various features of the drawings are not to-scale. On the contrary, the dimensions of the various features are arbitrarily expanded or reduced for clarity.

NOTATION AND NOMENCLATURE

Figure 1:
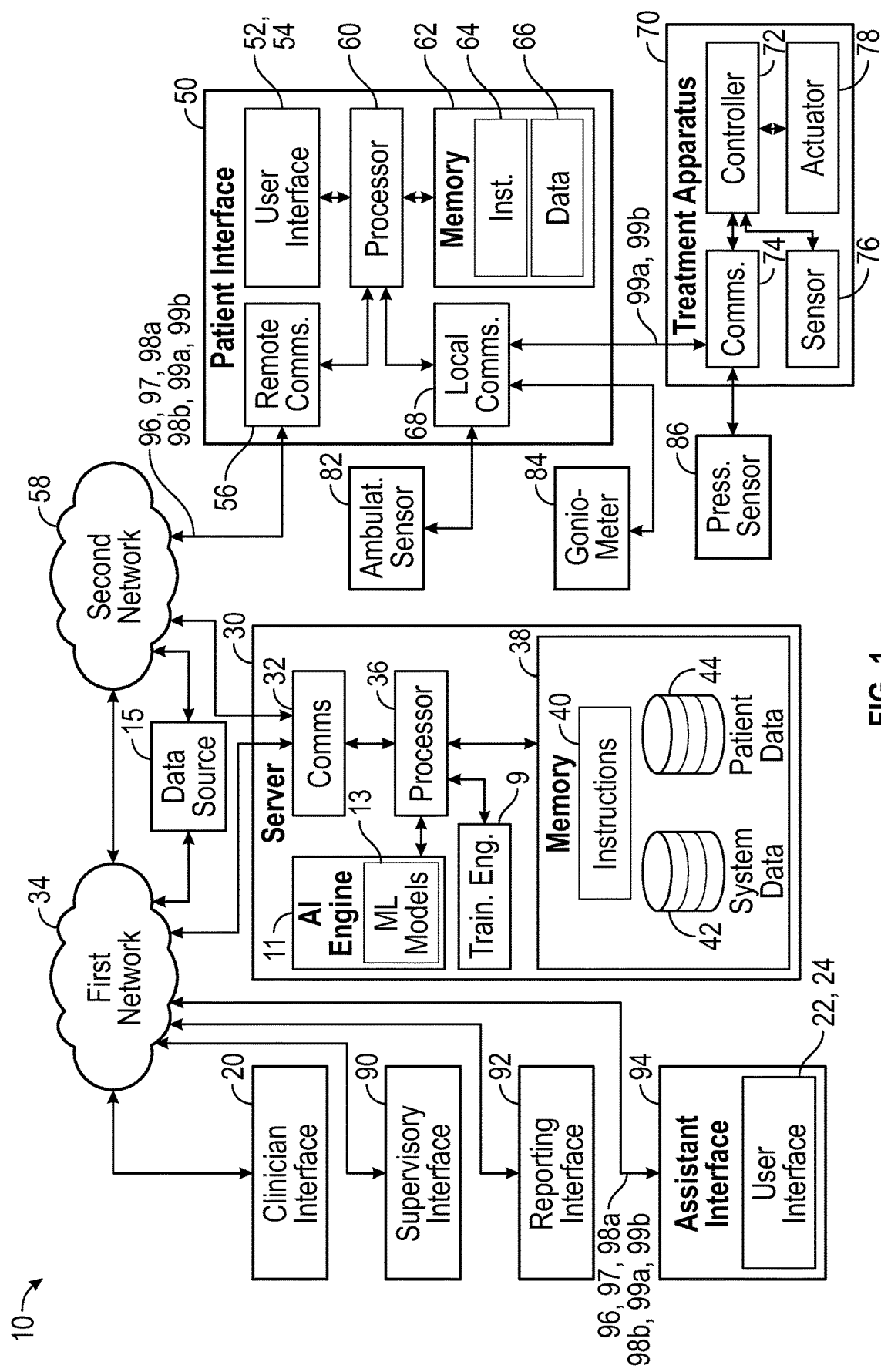
FIG. 1 generally illustrates a block diagram of an embodiment of a computer implemented system for managing a treatment plan according to principles of the present disclosure.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

In relation to electrical devices (whether standalone or as part of an integrated circuit), the terms "input" and "output" refer to electrical connections to the electrical devices, and shall not be read as verbs requiring action. For example, a differential amplifier (such as an operational amplifier) may have a first differential input and a second differential input, and these "inputs" define electrical connections to the operational amplifier, and shall not be read to require inputting signals to the operational amplifier.

"Assert" shall mean changing the state of a Boolean signal. Boolean signals may be asserted high or with a higher voltage, and Boolean signals may be asserted low or with a lower voltage, at the discretion of the circuit designer. Similarly, "de-assert" shall mean changing the state of the Boolean signal to a voltage level opposite the asserted state.

A processor can include various devices, including a controller. A "controller" shall mean, alone or in combination, individual circuit components, an application specific integrated circuit (ASIC), a microcontroller with controlling software, a digital signal processor (DSP), a processor with controlling software, or a field programmable gate array (FPGA), configured to read inputs and drive outputs responsive to the inputs.

Spatially relative terms, such as "inner," "outer," "beneath," "below," "lower," "above," "upper," "top," "bottom," "inside," "outside," "contained within," "superimposing upon," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

A "treatment plan" may include one or more treatment protocols, and each treatment protocol includes one or more treatment sessions. Each treatment session includes several session periods, with each session period including a particular exercise for treating the body part of the user. For example, a treatment plan for post-operative rehabilitation after a knee surgery may include an initial treatment protocol with twice daily stretching sessions for the first 3 days after surgery and a more intensive treatment protocol with active exercise sessions performed 4 times per day starting 4 days after surgery. A treatment plan may also include information pertaining to a medical procedure to perform on the user, a treatment protocol for the user using a treatment apparatus, a diet regimen for the user, a medication regimen for the user, a sleep regimen for the user, additional regimens, or some combination thereof.

An "infection probability" may include a likelihood of an infection as detected by a system or method described herein. For example, the infection probability may include a scale ranging from 0 (indicating a statistical certainty of no user infection) to 10 (indicating a statistical certainty of a user infection), with the infection probability increasing from 0 to 10. Alternatively, the infection probability may include a scale ranging from 0% (indicating a statistical certainty of no user infection) to 100% (indicating a statistical certainty of a user infection), with the infection probability increasing from 0% to 100%.

A "medical professional" may refer to a doctor, a physician, a physician's assistant, a physical therapist, a nurse (including a registered nurse or a nurse practitioner), a chiropractor, a dentist, acupuncturist, naturopath, physical trainer, coach, personal trainer, or the like. Alternatively, or in combination, a "medical professional" may refer to any person with a credential, license, degree, or the like in the field of medicine, physical therapy, rehabilitation, or the like.

A "healthcare administrator" may include a professional who coordinates with a medical professional, oversees administrative operations, or the like.

A "user" may include a person(s), patient(s), individual(s) using or interacting with a treatment apparatus, a medical professional, and/or a healthcare administrator.

The terms telemedicine, telehealth, telemed, teletherapeutic, etc. may be used interchangeably herein.

The terms "user infection" and "disease" may be used interchangeably herein and in the claim, and include secondary or refractory infections, malfunction, neoplasm, inability to function (e.g., removal, destruction by, e.g., a bullet or accident), attenuation of ability to function or of the integrity or the structure, and the like.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

When a user undergoes an invasive procedure (e.g., surgery) or otherwise experiences a breach of the patient's skin, the user can become infected with bacteria, such as at the location of the breach. Typically, the user will either self-diagnose or seek a consultation from a medical professionals. The consultation by the medical professionals generally requires an in-person, face-to-face, pre-arranged appointment with the user, where the medical professionals views a potential infection site of the user to assess whether the potential infection site is an infection. During a telehealth appointment, the medical professional may be able to remotely view the potential infection site of the user to determine a likelihood of the potential infection site being an actual infection (e.g., an infection probability). Depending on the infection probability of the user, an in-person appointment may or may not be necessary.

Determining an infection probability of a user and diagnosing a use infection may be a technically challenging problem. For example, when determining an infection probability, a multitude of information is considered, such as event information, temperature information, pressure information, discoloration information, image information, measurement information, pain information, pain level information, nerve problem information, any other desired information, or a combination thereof. The temperature information may include user temperature, and a subsequent comparison between the user temperature and a normal human temperature range (i.e., a temperature range for a healthy user or temperature below a threshold temperature). Alternatively, or in combination, the temperature information may include a comparison of the user temperature at a potential infected site and the user temperature at a corresponding non-infected site (e.g., the temperature of a potentially infected left knee of the user versus the temperature of a non-infected right knee of a user). Alternatively, or in combination, the temperature information may include a comparison of the user temperature and historical temperature data of other users (e.g., a temperature of a potential infected site of a user who underwent a surgical procedure versus a temperature, including, but not limited to, an average temperature of prior users who underwent the same surgical procedure as the user). The pressure information may include swelling (e.g., perceived swelling or an indication of swelling) of a potential infected site of a user. The discoloration information may include a change in color (e.g., redness or any abnormal color) of the user's skin at the potential infected site. Alternatively, or in combination, the discoloration information may include a comparison between a color of skin at the potential infected site and a color of skin at a corresponding non-infected site (e.g., the color of a potentially infected left knee of the user versus the color of a non-infected right knee of the user). The image information may include a still image or motion imagery (e.g., a video). As an example, the image information may include a comparison between an image of a user's body part before a surgical procedure and an image of the user's body part after the surgical procedure was conducted on the user's body part. The measurement information may include a size measurement of a potential infected site. For example, the measurement information may include sizing a two-dimensional area resulting from a skin breach. As another example, the measurement information may include a dimension, such as a length, of an incision from the event information. The event information may include etiological information, such as information pertaining to an invasive operation event (e.g., a surgical procedure) to a user or to an injury event (e.g., an accident, an intentional cut) to the user. In either event, the etiological information can be at least partially caused by a break, a cut, an opening, an open wound, or another form of a breach to the user's skin. The pain information may include, without limitation, information pertaining to the location or locus of pain experienced by the user, a change in the expressed or perceived level of that pain based on anatomical movements, tense or untensing of muscles, limb extensions or curls and the like. The pain level information may include, without limitation, information pertaining to the user's perceived experience of the intensity of any pain experienced with respect to pain information. Nerve problem information may include, without limitation, user experiences of tingling or neuropathies, of sharp or other types of nerve pain which appear to be neurological or neuromuscular in origin, of conduction issues related to the transmission of electrical impulses rendering an area especially tender, insensate or any level in between and of pain referred to other parts of the user's body.

Another challenge in determining infection probability and infection diagnosis is the collection of user information, or information provided by a user pertaining to the potential infected site. As non-limiting examples, user information may include an indication of a pressure, an indication of a pain level, an indication of a discoloration, and an indication of a mobility. User information may further include any of the information included in determining an infection probability, as set forth in [0033] hereinabove.

Further, another technical problem includes distally diagnosing, via a computing device, or interface (interchangeable with "computing device"), during a telemedicine or telehealth session, a user from a location different from a location at which the user is located. An additional technical problem may involve controlling or enabling the control of, from the different location, a treatment apparatus used by the user at the location at which the user is located. Oftentimes, when a user undergoes rehabilitative surgery (e.g., knee surgery), a medical professional may prescribe a treatment apparatus for the user to use to perform a treatment protocol at their residence or at any mobile location or temporary domicile.

Since a medical professional may be located in a location different from that of the user and the treatment apparatus, it may be technically challenging for the medical professional to monitor the user's actual progress (as opposed to relying on the user's word about their progress) using the treatment apparatus, modify the treatment plan according to the user's progress, adapt the treatment apparatus to the personal characteristics of the user as the user performs the treatment plan, and the like.

Each characteristic of the user, each result of a treatment plan, and each instantiation, modification or cancellation of a parameter, setting, configuration, etc. of the treatment apparatus may be timestamped and correlated with a particular step in the treatment plan. Such a technique may enable determining which steps in the treatment plan lead to desired results (e.g., improved muscle strength, range of motion, etc.) and which steps lead to diminishing returns (e.g., if continuing to exercise after 3 minutes actually delayed or harmed recovery).

Data may be collected from the treatment apparatuses and/or any suitable computing device (e.g., computing devices where personal information is entered, such as a clinician interface or user interface) over time as the user s use the system to perform the various treatment plans. The data that may be collected may include the characteristics of the users, the treatment plans performed by the user s, and the results of the treatment plans.

Embodiments of the present disclosure pertain to a system used to identify characteristics associated with a user infection. For example, the characteristics may include information received from a sensor (or sensors) and/or the user (including one or more user inputs). Additionally, the characteristics may include etiological information provided to the system by a computing system (e.g., a mobile device, a tablet device, a laptop computing device, a desktop computing device) with a user interface (e.g., a display) running a software application, or app, on the user interface. Using at least one of these characteristics, the system can generate an infection probability and/or diagnose a user infection. The diagnosis (of the user infection) may include, for example, a recommendation to apply a medication (e.g., an antibiotic such as penicillin, an antifungal, an antiviral, an anti-inflammatory, an ointment, some other infection-fighting substance, or some other health-improving or healing-promotion substance) to the infected site or, in alternative embodiments, through intramuscular ("IM"), intravenous ("IV"), sublingual, oral or other means of administration.

In some embodiments, the infection probability may be transmitted to various recipients, including the user, the medical professional, an insurance provider, a healthcare administrator, a power of attorney, and/or other third party. The transmission may include displaying an image on an interface, or otherwise communicating with a user through an interface. When the recipient is the user or the user's family or caregivers, the user or the user's family or caregivers can contact the medical professional, the insurance provider, the healthcare administrator, the power of attorney, and/or other third party to set up an appointment, such as a telemedicine-enabled appointment, and thereupon receive a treatment plan. When the recipient is one of the medical professional, the insurance provider, and the healthcare administrator, the recipient can contact the user and set up the appointment with the user to discuss the user's health condition and a treatment plan.

In some embodiments, the system can receive or generate a threshold infection probability. When the infection probability is at least at (i.e., at or above) the threshold infection probability, the system may determine that a recommended treatment plan is necessary. As a result, the recommendation can be transmitted with the infection probability. The recommendation may include at least one of a treatment plan for the user and a telemedicine-enabled appointment with the user to discuss to discuss a treatment plan. The recipient(s) of the recommendation may include any recipient, as set forth in [0039] hereinabove.

Some embodiments of the present disclosure pertain to diagnosing a user infection. For example, a system can use the information to identify a type of an infection incurred by the user. In some embodiments, a system can use information from the sensor(s) and/or the user to diagnose a potential infected site of the user. Additionally, the system may use event information, including etiological information, to diagnose the user infection. The diagnosed infection can be transmitted to a recipient, which may include any recipient, as set forth in [0039] hereinabove. The recipient can schedule a telemedicine-enabled appointment to discuss the infection diagnosis and a recommended treatment plan.

Some embodiments of the present disclosure pertain to using an artificial intelligence engine and/or machine learning engine to dynamically update the treatment plan based on sensor input information and/or user input information received by the system. For example, a user may undergo a treatment for a user infection. Subsequently, one or more characteristics pertaining to the user may be collected during or after the user performs the treatment plan. For example, temperature information, pressure information, discoloration information, image information, and measurement information may be collected from, for example, the potential infection site during or after the user performs the treatment plan. The artificial intelligence engine and/or machine learning engine can use the characteristics to determine whether the user infection is decreasing (i.e., the user is improving and/or the user infection is healing) or increasing (i.e., the user is not improving and/or the user infection is not healing or worsening) and thereupon modify the treatment plan for improved results.

The artificial intelligence engine and/or a machine learning engine may generate a modified treatment plan, which provides an updated treatment regimen for the user. For example, for an infection probability that is either increasing (relative to a previously generated infection probability) and/or equal to or exceeding a threshold infection, the modified treatment plan can generate one or more of a recommendation that includes additional and/or modified treatments (e.g., additional/modified medication, additional/modified recovery steps), a recommendation to set up a telemedicine-enabled appointment to discuss additional/modified treatments, or the like. Conversely, for an infection probability that is either decreasing (relative to a previously generated infection probability) or below a threshold infection, the modified treatment plan can recommend a modification to the treatments, such as a reduction/modification of medication, a reduction/modification of recovery procedures, a recommendation to set up a telemedicine-enabled appointment to discuss fewer/modified treatments, or the like.

In some embodiments, when a telemedicine-enabled appointment is recommended, the telemedicine-enabled appointment is automatically scheduled between a user or the user's family or caregivers and one or more of a medical professional, an insurance provider, and a healthcare administrator. For example, a system, an artificial intelligence engine, or a machine learning engine with calendar access privileges of the patient or the user's family or caregivers and the medical professional can review the respective calendars of the user or the user's family or caregivers and the medical professional, and populate (e.g., fill in) the telemedicine-enabled appointment into the respective calendars.

FIG. 1 generally illustrates a block diagram of a computer-implemented system 10, hereinafter called "the system" for managing a treatment plan according to principles of the present disclosure. Managing the treatment plan may include using an artificial intelligence engine to recommend treatment plans and/or to provide excluded treatment plans that should not be recommended to a user.

The system 10 also includes a server 30 configured to store and to provide data related to managing the treatment plan. The server 30 may include one or more computers and may take the form of a distributed and/or virtualized computer or computers. The server 30 may also include a first communication interface 32 configured to communicate with the clinician interface 20 via a first network 34. In some embodiments, the first network 34 may include wired and/or wireless network connections such as Wi-Fi, Bluetooth, ZigBee, Near-Field Communications (NFC), cellular data networks, etc. The server 30 may include a first processor 36 and a first machine-readable storage memory 38, which may be called a "memory" for short, holding first instructions 40 for performing the various actions of the server 30 for execution by the first processor 36. The server 30 is configured to store data regarding the treatment plan. For example, the memory 38 includes a system data store 42 configured to hold system data, such as data pertaining to treatment plans for treating one or more users. The server 30 is also configured to store data regarding performance by a user in following a treatment plan. For example, the memory 38 includes a user data store 44 configured to hold user data, such as data pertaining to the one or more users, including data representing each user's performance within the treatment plan.

In some embodiments, the server 30 may execute an artificial intelligence (AI) engine 11 that uses one or more machine learning models 13 to perform at least one of the embodiments disclosed herein. The server 30 may include a training engine 9 capable of generating the one or more machine learning models 13. Using one or more inputs (e.g., inputs from one or more sensors, inputs from a user) real-time data, and/or historical data correlations, the one or more machine learning models 13 may be trained to select treatment plans for user s, determine infection probabilities of user s, diagnose user infections, modify treatment plans for users, and control a treatment apparatus 70, among other things. The one or more machine learning models 13 may be generated by the training engine 9 and may be implemented in computer instructions executable by one or more processing devices of the training engine 9 and/or the server 30. To generate the one or more machine learning models 13, the training engine 9 may train the one or more machine learning models 13. The one or more machine learning models 13 may be used by the artificial intelligence engine 11.

The training engine 9 may be a rackmount server, a router computer, a personal computer, a portable digital assistant, a smartphone, a laptop computer, a tablet computer, a netbook, a desktop computer, an Internet of Things (IoT) device, any other desired computing device, or any combination of the above. The training engine 9 may be cloud-based or a real-time software platform, and it may include privacy software or protocols, and/or security software or protocols.

To train the one or more machine learning models 13, the training engine 9 may use a training data set of a corpus of the characteristics of multiple types of infections users can contract, the details (e.g., treatment protocol including the type of medications, amounts of each medication to apply to or use on or in the user, how often to treat the infection with medication, a schedule of exercises and rest periods, infection probability, wound size, parameters/configurations/settings of the treatment apparatus 70 throughout each step of the treatment plan, etc.) of the treatment plans performed by the users using the treatment apparatus 70, and the results of the treatment plans performed by the people. The one or more machine learning models 13 may be trained to match patterns of characteristics of a user with characteristics of other people in assigned to a particular cohort. The term "match" may refer to an exact match, a correlative match, a substantial match, etc. The one or more machine learning models 13 may be trained to receive the characteristics of a user as input, map the characteristics to characteristics of people assigned to a cohort, and select a treatment plan from that cohort. The one or more machine learning models 13 may also be trained to control, based on the treatment plan, the machine learning apparatus 70.

Different machine learning models 13 may be trained to recommend different treatment plans for different desired results. For example, one of the one or more machine learning models 13 may be trained to recommend treatment plans for most effective recovery, while another of the one or more machine learning models 13 may be trained to recommend treatment plans based on, for example, speed of recovery, cost of recovery, strength resulting from recovery, etc.

Using training data that includes training inputs and corresponding target outputs, the one or more machine learning models 13 may refer to model artifacts created by the training engine 9. The training engine 9 may find patterns in the training data wherein such patterns map the training input to the target output, and generate the machine learning models 13 that capture these patterns. In some embodiments, the artificial intelligence engine 11, the database 33, and/or the training engine 9 may reside on another component (e.g., assistant interface 94, clinician interface 20, etc.) depicted in FIG. 1.

The one or more machine learning models 13 may include, e.g., a single level of linear or non-linear operations (e.g., a support vector machine [SVM]) or the machine learning models 13 may be a deep network, i.e., a machine learning model including multiple levels of non-linear operations. Examples of deep networks are neural networks including generative adversarial networks, convolutional neural networks, recurrent neural networks with one or more hidden layers, and fully connected neural networks (e.g., each neuron may transmit its output signal to the input of the remaining neurons, as well as to itself). For example, the machine learning model may include numerous layers and/or hidden layers that perform calculations (e.g., dot products) using various neurons.

The system 10 also includes a user interface 50 configured to communicate information to a user and to receive feedback from the user. Specifically, the user interface includes an input device 52 and an output device 54, which may be collectively called a user interface 52, 54. The input device 52 may include one or more devices, such as a keyboard, a mouse, a touchscreen input, a gesture sensor (including sensors for eye blinking used to communicate), a haptic device, and/or a microphone and processor configured for voice recognition. The output device 54 may take one or more different forms including, for example, a computer monitor or display screen on a tablet, smartphone, or a smartwatch. The output device 54 may include other hardware and/or software components such as a projector, virtual reality capability, augmented reality capability, etc. The output device 54 may incorporate various different visual, audio, or other sensorial or presentation technologies. For example, the output device 54 may include a non-visual display, such as an audio signal, which may include spoken language and/or other sounds such as tones, chimes, and/or melodies, which may signal different conditions and/or directions. The output device 54 may include one or more different display screens presenting various data and/or interfaces or controls for use by the user. The output device 54 may include graphics, which may be presented by a web-based interface and/or by a computer program or application ("app").

As shown in FIG. 1, the user interface 50 includes a second communication interface 56, which may also be called a remote communication interface configured to communicate with the server 30 and/or the clinician interface 20 via a second network 58. In some embodiments, the second network 58 may include a local area network (LAN), such as an Ethernet network. In some embodiments, the second network 58 may include an Intranet or Intranets and/or the Internet and/or a virtual private network (VPN), and communications between the user interface 50 and the server 30 and/or the clinician interface 20 may be secured via encryption, such as, for example, encryption mediated by using a VPN. In some embodiments, the second network 58 may include wired and/or wireless network connections such as Wi-Fi, Bluetooth, ZigBee, Near-Field Communications (NFC), cellular data networks, etc. In some embodiments, the second network 58 may be the same as and/or operationally coupled to the first network 34.

The user interface 50 includes a second processor 60 and a second machine-readable storage memory 62 holding second instructions 64 for execution by the second processor 60 for performing various actions of user interface 50. The second machine-readable storage memory 62 also includes a local data store 66 configured to hold data, such as data pertaining to a treatment plan and/or user data, such as data representing a user's performance within a treatment plan. The user interface 50 also includes a local communication interface 68 configured to communicate with various devices for use by the user in the vicinity of the user interface 50. The local communication interface 68 may include wired and/or wireless communications. In some embodiments, the local communication interface 68 may include a local wireless network such as Wi-Fi, Bluetooth, ZigBee, Near-Field Communications (NFC), cellular data networks, etc.

The system 10 also includes a treatment apparatus 70 configured to be manipulated by the user and/or to manipulate a body part of the user for performing activities according to the treatment plan. In some embodiments, the treatment apparatus 70 may take the form of an exercise and rehabilitation apparatus configured to perform and/or to aid in the performance of a rehabilitation regimen, which may be or include an orthopedic rehabilitation regimen, and the treatment includes rehabilitation of a body part of the user, such as a joint and/or a bone and/or a tendon and/or a ligament and/or a muscle group. The treatment apparatus 70 may be any suitable medical, rehabilitative, therapeutic, etc. apparatus configured to be controlled distally via another computing device to treat a user and/or exercise the user, and such exercise or treatment may also include taking and analyzing and/or storing measurements of neurological or neuromuscular aspects of the user or the user's performance as well as of vital signs of the user. The treatment apparatus 70 may be an electromechanical machine including one or more weights, an electromechanical bicycle, an electromechanical spin-wheel, a smart-mirror, a treadmill, or the like. The body part may include, for example, a spine, a hand, a foot, a knee, or a shoulder. The body part may include a part of a joint, a bone, or a muscle group, such as one or more vertebrae, a tendon, or a ligament. As shown in FIG. 1, the treatment apparatus 70 includes a controller 72, which may include one or more processors, computer memory, and/or other components. The treatment apparatus 70 also includes a fourth communication interface 74 configured to communicate with the user interface 50 via the local communication interface 68. The treatment apparatus 70 also includes one or more internal sensors 76 and an actuator 78, such as a motor. The actuator 78 may be used, for example, for moving the user's body part and/or for resisting forces by the user.

The internal sensors 76 may measure one or more operating characteristics of the treatment apparatus 70 such as, for example, a force, a position, a speed, and/or a velocity. In some embodiments, the internal sensors 76 may include a position sensor configured to measure at least one of a linear motion or an angular motion of a body part of the user. For example, an internal sensor 76 in the form of a position sensor may measure a distance that (or a time in which) the user is able to move a part of the treatment apparatus 70, where such distance (or time) may correspond to a range of motion that the user's body part is able to achieve. In some embodiments, the internal sensors 76 may include a force sensor configured to measure a force applied by the user. For example, an internal sensor 76 in the form of a force sensor may measure a force or weight the user is able to apply, using a particular body part, to the treatment apparatus 70.

The system 10 shown in FIG. 1 also includes an ambulation sensor 82, which communicates with the server 30 via the local communication interface 68 of the user interface 50. The ambulation sensor 82 may track and store a number of steps taken by the user. In some embodiments, the ambulation sensor 82 may take the form of a wristband, wristwatch, or smart watch. In some embodiments, the ambulation sensor 82 may be integrated within a phone, such as a smartphone.

The system 10 shown in FIG. 1 also includes a goniometer 84, which communicates with the server 30 via the local communication interface 68 of the user interface 50. The goniometer 84 measures an angle of the user's body part. For example, the goniometer 84 may measure the angle of flex of a user's knee or elbow or shoulder.

The system 10 shown in FIG. 1 also includes a pressure sensor 86, which communicates with the server 30 via the local communication interface 68 of the user interface 50. The pressure sensor 86 measures an amount of pressure or weight applied by a body part of the user. For example, pressure sensor 86 may measure an amount of force applied by a user's foot when pedaling a stationary bike.

The system 10 shown in FIG. 1 also includes a supervisory interface 90 which may be similar or identical to the clinician interface 20. In some embodiments, the supervisory interface 90 may have enhanced functionality beyond what is provided on the clinician interface 20. The supervisory interface 90 may be configured for use by a medical professional having responsibility for the treatment plan, such as an orthopedic surgeon.

The system 10 shown in FIG. 1 also includes a reporting interface 92 which may be similar or identical to the clinician interface 20. In some embodiments, the reporting interface 92 may have less functionality from what is provided on the clinician interface 20. For example, the reporting interface 92 may not have the ability to modify a treatment plan. Such a reporting interface 92 may be used, for example, by a biller to determine the use of the system 10 for billing purposes. In another example, the reporting interface 92 may not have the ability to display user identifiable information, presenting only pseudonymized data and/or anonymized data for certain data fields concerning a data subject and/or for certain data fields concerning a quasi-identifier of the data subject. Such a reporting interface 92 may be used, for example, by a researcher to determine various effects of a treatment plan on different users.

The system 10 includes an assistant interface 94 for an assistant, such as a doctor, a nurse, a physical therapist, or a technician, to remotely communicate with the user interface 50 and/or the treatment apparatus 70. Such remote communications may enable the assistant to provide assistance or guidance to a user using the system 10. More specifically, the assistant interface 94 is configured to communicate a telemedicine signal 96, 97, 98a, 98b, 99a, 99b with the user interface 50 via a network connection such as, for example, via the first network 34 and/or the second network 58. The telemedicine signal 96, 97, 98a, 98b, 99a, 99b includes one of an audio signal 96, an audiovisual signal 97, an interface control signal 98a for controlling a function of the user interface 50, an interface monitor signal 98b for monitoring a status of the user interface 50, an apparatus control signal 99a for changing an operating parameter of the treatment apparatus 70, and/or an apparatus monitor signal 99b for monitoring a status of the treatment apparatus 70. In some embodiments, each of the control signals 98a, 99a may be unidirectional, conveying commands from the assistant interface 94 to the user interface 50. In some embodiments, in response to successfully receiving a control signal 98a, 99a and/or to communicate successful and/or unsuccessful implementation of the requested control action, an acknowledgement message may be sent from the user interface 50 to the assistant interface 94. In some embodiments, each of the monitor signals 98b, 99b may be unidirectional, status-information commands from the user interface 50 to the assistant interface 94. In some embodiments, an acknowledgement message may be sent from the assistant interface 94 to the user interface 50 in response to successfully receiving one of the monitor signals 98b, 99b.

In some embodiments, the user interface 50 may be configured as a pass-through for the apparatus control signals 99a and the apparatus monitor signals 99b between the treatment apparatus 70 and one or more other devices, such as the assistant interface 94 and/or the server 30. For example, the user interface 50 may be configured to transmit an apparatus control signal 99a in response to an apparatus control signal 99a within the telemedicine signal 96, 97, 98a, 98b, 99a, 99b from the assistant interface 94.

In some embodiments, the assistant interface 94 may be presented on a shared physical device as the clinician interface 20. For example, the clinician interface 20 may include one or more screens that implement the assistant interface 94. Alternatively or additionally, the clinician interface 20 may include additional hardware components, such as a video camera, a speaker, and/or a microphone, to implement aspects of the assistant interface 94.

In some embodiments, one or more portions of the telemedicine signal 96, 97, 98a, 98b, 99a, 99b may be generated from a prerecorded source (e.g., an audio recording, a video recording, or an animation) for presentation by the output device 54 of the user interface 50. For example, a tutorial video may be streamed from the server 30 and presented upon the user interface 50. Content from the prerecorded source may be requested by the user via the patient interface 50. Alternatively, via a control on the assistant interface 94, the assistant may cause content from the prerecorded source to be played on the user interface 50.

The assistant interface 94 includes an assistant input device 22 and an assistant display 24, which may be collectively called an assistant user interface 22, 24. The assistant input device 22 may include one or more of a telephone, a keyboard, a mouse, a trackpad, or a touch screen, for example. Alternatively or additionally, the assistant input device 22 may include one or more microphones. In some embodiments, the one or more microphones may take the form of a telephone handset, headset, or wide-area microphone or microphones configured for the assistant to speak to a user via the user interface 50. In some embodiments, assistant input device 22 may be configured to provide voice-based functionalities, with hardware and/or software configured to interpret spoken instructions by the assistant by using the one or more microphones. The assistant input device 22 may include functionality provided by or similar to existing voice-based assistants such as Siri by Apple, Alexa by Amazon, Google Assistant, or Bixby by Samsung. The assistant input device 22 may include other hardware and/or software components. The assistant input device 22 may include one or more general purpose devices and/or special-purpose devices.

The assistant display 24 may take one or more different forms including, for example, a computer monitor or display screen on a tablet, a smartphone, or a smart watch. The assistant display 24 may include other hardware and/or software components such as projectors, virtual reality capabilities, or augmented reality capabilities, etc. The assistant display 24 may incorporate various different visual, audio, or other presentation technologies. For example, the assistant display 24 may include a non-visual display, such as an audio signal, which may include spoken language and/or other sounds such as tones, chimes, melodies, and/or compositions, which may signal different conditions and/or directions. The assistant display 24 may include one or more different display screens presenting various data and/or interfaces or controls for use by the assistant. The assistant display 24 may include graphics, which may be presented by a web-based interface and/or by a computer program or application.

In some embodiments, the system 10 may provide computer translation of language from the assistant interface 94 to the user interface 50 and/or vice-versa. The computer translation of language may include computer translation of spoken language and/or computer translation of text. Additionally or alternatively, the system 10 may provide voice recognition and/or spoken pronunciation of text. For example, the system 10 may convert spoken words to printed text and/or the system 10 may audibly speak language from printed text. The system 10 may be configured to recognize spoken words by any or all of the user, the clinician, and/or the assistant. In some embodiments, the system 10 may be configured to recognize and react to spoken requests or commands by the user. For example, the system 10 may automatically initiate a telemedicine session in response to a verbal command by the user (which may be given in any one of several different languages).

In some embodiments, the server 30 may generate aspects of the assistant display 24 for presentation by the assistant interface 94. For example, the server 30 may include a web server configured to generate the display screens for presentation upon the assistant display 24. For example, the artificial intelligence engine 11 may generate recommended treatment plans and/or excluded treatment plans for users and generate the display screens including those recommended treatment plans and/or external treatment plans for presentation on the assistant display 24 of the assistant interface 94. In some embodiments, the assistant display 24 may be configured to present a virtualized desktop hosted by the server 30. In some embodiments, the server 30 may be configured to communicate with the assistant interface 94 via the first network 34. In some embodiments, the first network 34 may include a local area network (LAN), such as an Ethernet network. In some embodiments, the first network 34 may include the Internet, and communications between the server 30 and the assistant interface 94 may be secured via privacy enhancing technologies, such as, for example, by using encryption over a virtual private network (VPN). Alternatively or additionally, the server 30 may be configured to communicate with the assistant interface 94 via one or more networks independent of the first network 34 and/or other communication means, such as a direct wired or wireless communication channel. In some embodiments, the user interface 50 and the treatment apparatus 70 may each operate from a user location geographically separate from a location of the assistant interface 94. For example, the user interface 50 and the treatment apparatus 70 may be used as part of an in-home rehabilitation system, which may be aided remotely by using the assistant interface 94 at a centralized location, such as a clinic or a call center.

In some embodiments, the assistant interface 94 may be one of several different terminals (e.g., computing devices) that may be grouped together, for example, in one or more call centers or at one or more clinicians' offices. In some embodiments, a plurality of assistant interfaces 94 may be distributed geographically. In some embodiments, a person (e.g., medical professional) may work as an assistant remotely from any conventional office infrastructure. Such remote work may be performed, for example, where the assistant interface 94 takes the form of a computer and/or telephone. This remote work functionality may allow for work-from-home arrangements that may include part time and/or flexible work hours for an assistant.

Figure 2:
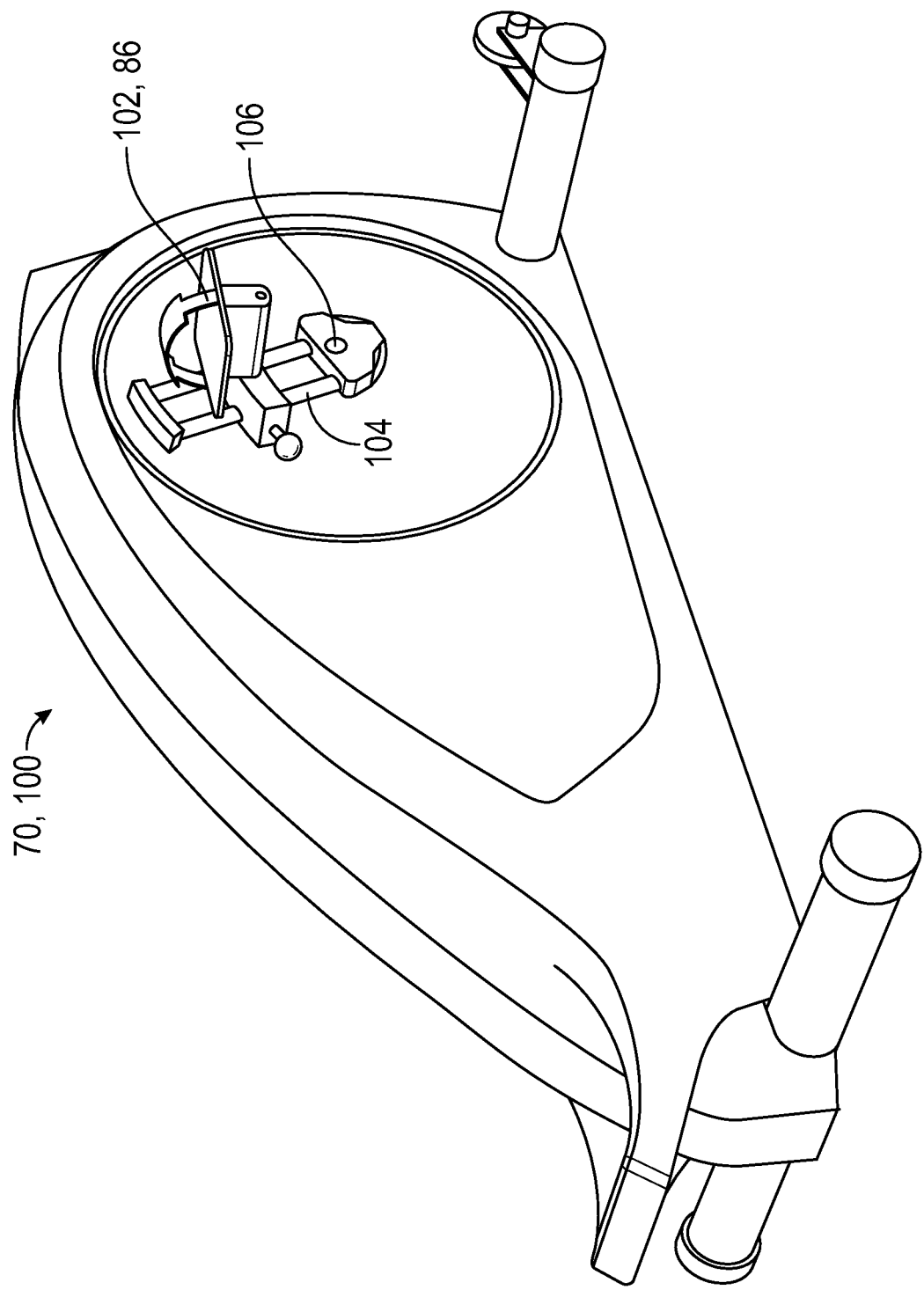
FIGS. 2-3 generally illustrate an embodiment of a treatment apparatus according to principles of the present disclosure.
Figure 3:
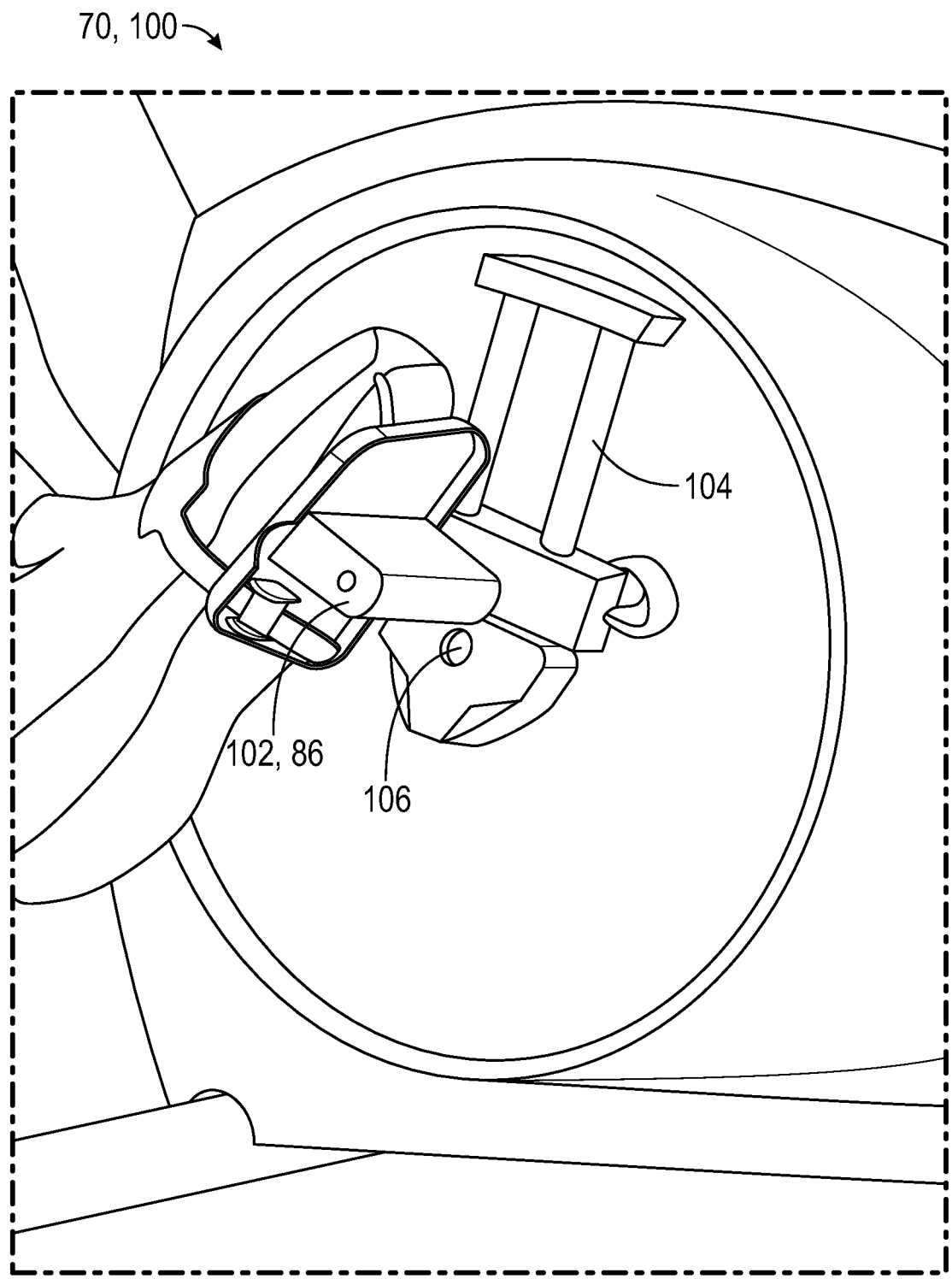

FIGS. 2-3 generally illustrate an embodiment of a treatment apparatus 70 according to principles of the present disclosure. More specifically, FIG. 2 shows a treatment apparatus 70 in the form of a stationary cycling machine 100, which may be called a stationary bike, for short. The stationary cycling machine 100 includes a set of pedals 102 each attached to a pedal arm 104 for rotation about an axle 106. In some embodiments, and as shown in FIG. 2, the pedals 102 are movable on the pedal arms 104 in order to adjust a range of motion used by the user in pedaling. For example, the pedals being located inwardly toward the axle 106 corresponds to a smaller range of motion than when the pedals are located outwardly away from the axle 106. A pressure sensor 86 is attached to or embedded within one of the pedals 102 for measuring an amount of force applied by the user on the pedal 102. The pressure sensor 86 may communicate wirelessly to the treatment apparatus 70 and/or to the user interface 50.

Figure 4:
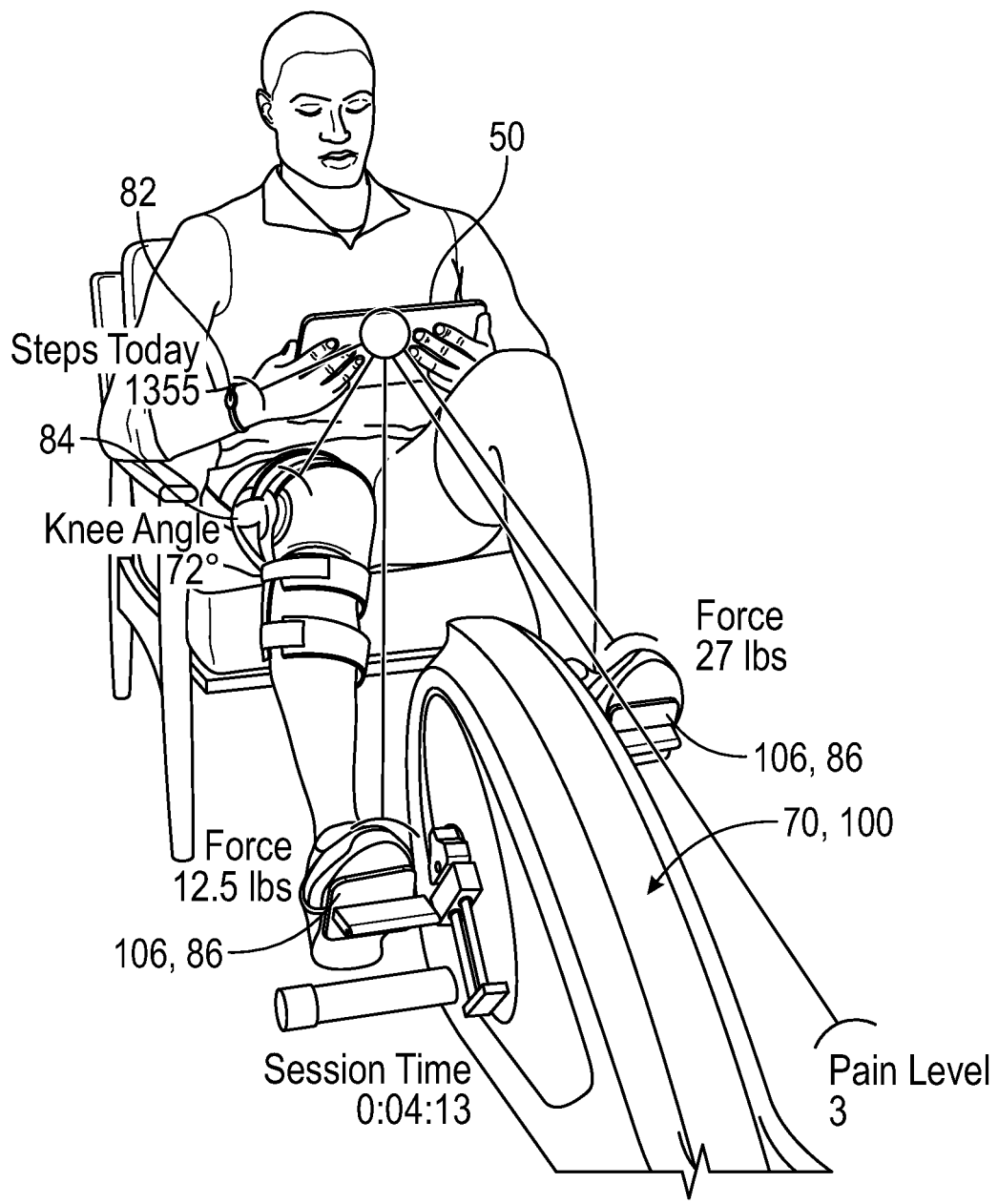
FIG. 4 generally illustrates a user using the treatment apparatus of FIGS. 2 and 3, and shows sensors and various data parameters connected to a user interface according to principles of the present disclosure.

FIG. 4 generally illustrates a user using the treatment apparatus of FIGS. 2 and 3, and showing sensors and various data parameters connected to a user interface 50 according to principles of the present disclosure. The example user interface 50 is a tablet computer or smartphone, or a phablet, such as an iPad, an iPhone, an Android device, or a Surface tablet, which is held manually by the user. In some other embodiments, the user interface 50 may be embedded within or attached to the treatment apparatus 70. FIG. 4 shows the user wearing the ambulation sensor 82 on his wrist, with a note showing "STEPS TODAY 1355", indicating that the ambulation sensor 82 has recorded and transmitted that step count to the user interface 50. FIG. 4 also shows the user wearing the goniometer 84 on his right knee, with a note showing "KNEE ANGLE 72°", indicating that the goniometer 84 is measuring and transmitting that knee angle to the user interface 50. FIG. 4 also shows a right side of one of the pedals 102 with a pressure sensor 86 showing "FORCE 12.5 lbs.", indicating that the right pedal pressure sensor 86 is measuring and transmitting that force measurement to the user interface 50. FIG. 4 also shows a left side of one of the pedals 102 with a pressure sensor 86 showing "FORCE 27 lbs.", indicating that the left pedal pressure sensor 86 is measuring and transmitting that force measurement to the user interface 50. FIG. 4 also shows other user data, such as an indicator of "SESSION TIME 0:04:13", indicating that the user has been using the treatment apparatus 70 for 4 minutes and 13 seconds. This session time may be determined by the user interface 50 based on information received from the treatment apparatus 70. FIG. 4 also shows an indicator showing "PAIN LEVEL 3". Such a pain level may be obtained from the user in response to a solicitation, such as a question, presented upon the user interface 50.

Figure 5:
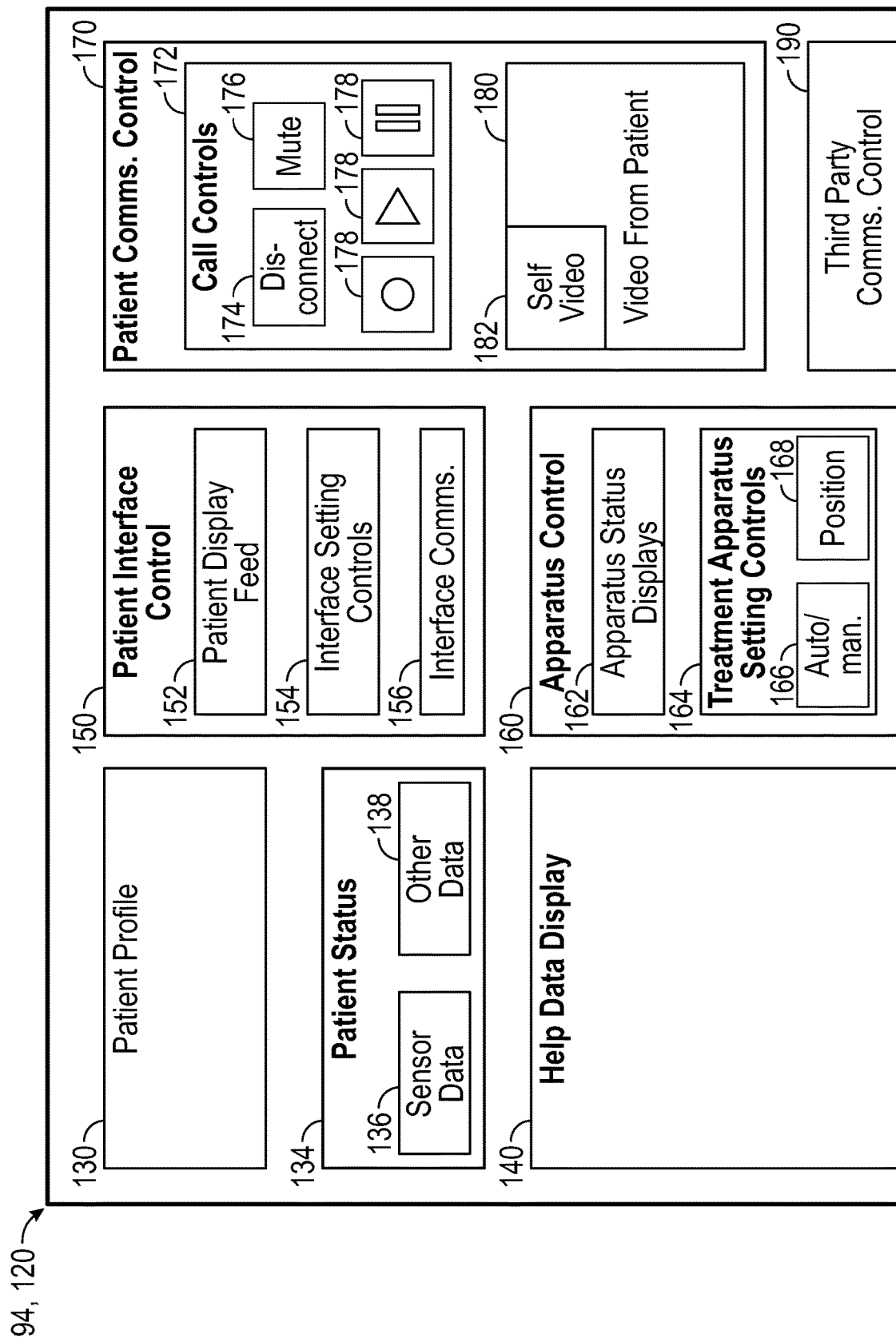
FIG. 5 generally illustrates an example embodiment of an overview display of an assistant interface according to principles of the present disclosure.

FIG. 5 generally illustrates an overview display 120 of the assistant interface 94 according to principles of the present disclosure. Specifically, the overview display 120 presents several different controls and interfaces for the assistant to remotely assist a user with using the user interface 50 and/or the treatment apparatus 70. This remote assistance functionality may also be called telemedicine or telehealth.

Specifically, the overview display 120 includes a user profile display 130 presenting biographical information regarding a user using the treatment apparatus 70. The user profile display 130 may take the form of a portion or region of the overview display 120, as shown in FIG. 5, although the user profile display 130 may take other forms, such as a separate screen or a popup window. In some embodiments, the user profile display 130 may include a limited subset of the user's biographical information. More specifically, the data presented upon the user profile display 130 may depend upon the assistant's need for that information. For example, a medical professional that is assisting the user with a medical issue may be provided with medical history information regarding the user, whereas a technician troubleshooting an issue with the treatment apparatus 70 may be provided with a much more limited set of information regarding the user. The technician, for example, may be given only the user's name. The user profile display 130 may include pseudonymized data and/or anonymized data or use any privacy enhancing technology to prevent confidential user data from being communicated in a way that could violate user confidentiality requirements. Such privacy enhancing technologies may enable compliance with laws, regulations, or other rules of governance such as, but not limited to, the Health Insurance Portability and Accountability Act (HIPAA), or the General Data Protection Regulation (GDPR), wherein the user may be deemed a "data subject."

In some embodiments, the user profile display 130 may present information regarding the treatment plan for the user to follow in using the treatment apparatus 70. Such treatment plan information may be limited to an assistant who is a medical professional, such as a doctor or physical therapist. For example, a medical professional assisting the user with an issue regarding the treatment regimen may be provided with treatment plan information, whereas a technician troubleshooting an issue with the treatment apparatus 70 may not be provided with any information regarding the user's treatment plan.

In some embodiments, one or more recommended treatment plans and/or excluded treatment plans may be presented in the user profile display 130 to the assistant. The one or more recommended treatment plans and/or excluded treatment plans may be generated by the artificial intelligence engine 11 of the server 30 and received from the server 30 in real-time during, inter alia, a telemedicine or telehealth session.

The example overview display 120 shown in FIG. 5 also includes a user status display 134 presenting status information regarding a user using the treatment apparatus. The user status display 134 may take the form of a portion or region of the overview display 120, as shown in FIG. 5, although the user status display 134 may take other forms, such as a separate screen or a popup window. The user status display 134 includes sensor data 136 from one or more of the external sensors 82, 84, 86, and/or from one or more internal sensors 76 of the treatment apparatus 70. In some embodiments, the user status display 134 may present other data 138 regarding the user, such as last reported pain level, or progress within a treatment plan.

User access controls may be used to limit access, including what data is available to be viewed and/or modified, on any or all of the user interfaces 20, 50, 90, 92, 94 of the system 10. In some embodiments, user access controls may be employed to control what information is available to any given person using the system 10. For example, data presented on the assistant interface 94 may be controlled by user access controls, with permissions set depending on the assistant/user's need for and/or qualifications to view that information.

The example overview display 120 shown in FIG. 5 also includes a help data display 140 presenting information for the assistant to use in assisting the user. The help data display 140 may take the form of a portion or region of the overview display 120, as shown in FIG. 5. The help data display 140 may take other forms, such as a separate screen or a popup window. The help data display 140 may include, for example, presenting answers to frequently asked questions regarding use of the user interface 50 and/or the treatment apparatus 70. The help data display 140 may also include research data or best practices. In some embodiments, the help data display 140 may present scripts for answers or explanations in response to user questions. In some embodiments, the help data display 140 may present flow charts or walk-throughs for the assistant to use in determining a root cause and/or solution to a user's problem. In some embodiments, the assistant interface 94 may present two or more help data displays 140, which may be the same or different, for simultaneous presentation of help data for use by the assistant. for example, a first help data display may be used to present a troubleshooting flowchart to determine the source of a user's problem, and a second help data display may present script information for the assistant to read to the user, such information to preferably include directions for the user to perform some action, which may help to narrow down or solve the problem. In some embodiments, based upon inputs to the troubleshooting flowchart in the first help data display, the second help data display may automatically populate with script information.

The example overview display 120 shown in FIG. 5 also includes a user interface control 150 presenting information regarding the user interface 50, and/or to modify one or more settings of the user interface 50. The user interface control 150 may take the form of a portion or region of the overview display 120, as shown in FIG. 5. The user interface control 150 may take other forms, such as a separate screen or a popup window. The user interface control 150 may present information communicated to the assistant interface 94 via one or more of the interface monitor signals 98b. As shown in FIG. 5, the user interface control 150 includes a display feed 152 of the display presented by the user interface 50. In some embodiments, the display feed 152 may include a live copy of the display screen currently being presented to the user by the user interface 50. In other words, the display feed 152 may present an image of what is presented on a display screen of the user interface 50. In some embodiments, the display feed 152 may include abbreviated information regarding the display screen currently being presented by the user interface 50, such as a screen name or a screen number. The user interface control 150 may include a user interface setting control 154 for the assistant to adjust or to control one or more settings or aspects of the user interface 50. In some embodiments, the user interface setting control 154 may cause the assistant interface 94 to generate and/or to transmit an interface control signal 98 for controlling a function or a setting of the user interface 50.

In some embodiments, the user interface setting control 154 may include collaborative browsing or co-browsing capability for the assistant to remotely view and/or control the user interface 50. For example, the user interface setting control 154 may enable the assistant to remotely enter text to one or more text entry fields on the user interface 50 and/or to remotely control a cursor on the user interface 50 using a mouse or touchscreen of the assistant interface 94.

In some embodiments, using the user interface 50, the user interface setting control 154 may allow the assistant to change a setting that cannot be changed by the user. For example, the user interface 50 may be precluded from accessing a language setting to prevent a user from inadvertently switching, on the user interface 50, the language used for the displays, whereas the user interface setting control 154 may enable the assistant to change the language setting of the user interface 50. In another example, the user interface 50 may not be able to change a font size setting to a smaller size in order to prevent a user from inadvertently switching the font size used for the displays on the user interface 50 such that the display would become illegible to the user, whereas the user interface setting control 154 may provide for the assistant to change the font size setting of the user interface 50.

The example overview display 120 shown in FIG. 5 also includes an interface communications display 156 showing the status of communications between the user interface 50 and one or more other devices 70, 82, 84, such as the treatment apparatus 70, the ambulation sensor 82, and/or the goniometer 84. The interface communications display 156 may take the form of a portion or region of the overview display 120, as shown in FIG. 5. The interface communications display 156 may take other forms, such as a separate screen or a popup window. The interface communications display 156 may include controls for the assistant to remotely modify communications with one or more of the other devices 70, 82, 84. For example, the assistant may remotely command the user interface 50 to reset communications with one of the other devices 70, 82, 84, or to establish communications with a new one of the other devices 70, 82, 84. This functionality may be used, for example, where the user has a problem with one of the other devices 70, 82, 84, or where the user receives a new or a replacement one of the other devices 70, 82, 84.

The example overview display 120 shown in FIG. 5 also includes an apparatus control 160 for the assistant to view and/or to control information regarding the treatment apparatus 70. The apparatus control 160 may take the form of a portion or region of the overview display 120, as shown in FIG. 5. The apparatus control 160 may take other forms, such as a separate screen or a popup window. The apparatus control 160 may include an apparatus status display 162 with information regarding the current status of the apparatus. The apparatus status display 162 may present information communicated to the assistant interface 94 via one or more of the apparatus monitor signals 99b. The apparatus status display 162 may indicate whether the treatment apparatus 70 is currently communicating with the user interface 50. The apparatus status display 162 may present other current and/or historical information regarding the status of the treatment apparatus 70.

The apparatus control 160 may include an apparatus setting control 164 for the assistant to adjust or control one or more aspects of the treatment apparatus 70. The apparatus setting control 164 may cause the assistant interface 94 to generate and/or to transmit an apparatus control signal 99 for changing an operating parameter of the treatment apparatus 70, (e.g., a pedal radius setting, a resistance setting, a target RPM, etc.). The apparatus setting control 164 may include a mode button 166 and a position control 168, which may be used in conjunction for the assistant to place an actuator 78 of the treatment apparatus 70 in a manual mode, after which a setting, such as a position or a speed of the actuator 78, can be changed using the position control 168. The mode button 166 may provide for a setting, such as a position, to be toggled between automatic and manual modes. In some embodiments, one or more settings may be adjustable at any time, and without having an associated auto/manual mode. In some embodiments, the assistant may change an operating parameter of the treatment apparatus 70, such as a pedal radius setting, while the user is actively using the treatment apparatus 70. Such "on the fly" adjustment may or may not be available to the user using the user interface 50. In some embodiments, the apparatus setting control 164 may allow the assistant to change a setting that cannot be changed by the user using the user interface 50. For example, the user interface 50 may be precluded from changing a preconfigured setting, such as a height or a tilt setting of the treatment apparatus 70, whereas the apparatus setting control 164 may provide for the assistant to change the height or tilt setting of the treatment apparatus 70.

The example overview display 120 shown in FIG. 5 also includes a user communications control 170 for controlling an audio or an audiovisual communications session with the user interface 50. The communications session with the user interface 50 may include a live feed from the assistant interface 94 for presentation by the output device of the user interface 50. The live feed may take the form of an audio feed and/or a video feed. In some embodiments, the user interface 50 may be configured to provide two-way audio or audiovisual communications with a person using the assistant interface 94. Specifically, the communications session with the user interface 50 may include bidirectional (two-way) video or audiovisual feeds, with each of the user interface 50 and the assistant interface 94 presenting video of the other one. In some embodiments, the user interface 50 may present video from the assistant interface 94, while the assistant interface 94 presents only audio or the assistant interface 94 presents no live audio or visual signal from the patient interface 50. In some embodiments, the assistant interface 94 may present video from the user interface 50, while the user interface 50 presents only audio or the user interface 50 presents no live audio or visual signal from the assistant interface 94.

In some embodiments, the audio or an audiovisual communications session with the user interface 50 may take place, at least in part, while the user is performing the rehabilitation regimen upon the body part. The user communications control 170 may take the form of a portion or region of the overview display 120, as shown in FIG. 5. The user communications control 170 may take other forms, such as a separate screen or a popup window. The audio and/or audiovisual communications may be processed and/or directed by the assistant interface 94 and/or by another device or devices, such as a telephone system, or a videoconferencing system used by the assistant while the assistant uses the assistant interface 94. Alternatively or additionally, the audio and/or audiovisual communications may include communications with a third party. For example, the system 10 may enable the assistant to initiate a 3-way conversation regarding use of a particular piece of hardware or software, with the user and a subject matter expert, such as a medical professional or a specialist. The example user communications control 170 shown in FIG. 5 includes call controls 172 for the assistant to use in managing various aspects of the audio or audiovisual communications with the user. The call controls 172 include a disconnect button 174 for the assistant to end the audio or audiovisual communications session. The call controls 172 also include a mute button 176 to temporarily silence an audio or audiovisual signal from the assistant interface 94. In some embodiments, the call controls 172 may include other features, such as a hold button (not shown). The call controls 172 also include one or more record/playback controls 178, such as record, play, and pause buttons to control, with the user interface 50, recording and/or playback of audio and/or video from the teleconference session. The call controls 172 also include a video feed display 180 for presenting still and/or video images from the user interface 50, and a self-video display 182 showing the current image of the assistant using the assistant interface. The self-video display 182 may be presented as a picture-in-picture format, within a section of the video feed display 180, as shown in FIG. 5. Alternatively or additionally, the self-video display 182 may be presented separately and/or independently from the video feed display 180.

The example overview display 120 shown in FIG. 5 also includes a third party communications control 190 for use in conducting audio and/or audiovisual communications with a third party. The third party communications control 190 may take the form of a portion or region of the overview display 120, as shown in FIG. 5. The third party communications control 190 may take other forms, such as a display on a separate screen or a popup window. The third party communications control 190 may include one or more controls, such as a contact list and/or buttons or controls to contact a third party regarding use of a particular piece of hardware or software, e.g., a subject matter expert, such as a medical professional or a specialist. The third party communications control 190 may include conference calling capability for the third party to simultaneously communicate with both the assistant via the assistant interface 94, and with the user via the user interface 50. For example, the system 10 may provide for the assistant to initiate a 3-way conversation with the user and the third party.

Sensors can be used to monitor the user and provide one or more inputs to the system 10 described in FIG. 1 through either a wired connection or a wireless network (e.g., the first communications interface 32, the second communications interface 56, the first network 34, or the second network 58). The system 10 can subsequently analyze the one or more inputs to determine an infection probability or diagnose a user infection, as non-limiting examples. For example, sensing devices 600*a*, 600*b*, and 600*c* generally illustrated in FIGS. 6A, 6B, and 6C, respectively, detect environmental stimuli and convert the environmental stimuli into one or more electrical signals (e.g., digital or analog) that are transmitted to a processing device. In this regard, the sensing devices 600*a*, 600*b*, and 600*c* can provide information used to identify characteristics associated with a user infection. Accordingly, the sensing devices 600*a*, 600*b*, 600*c* generally illustrated and described in FIGS. 6A, 6B, and 6C, respectively, can be used to determine an infection probability and/or diagnose a user infection. The sensing devices 600*a*, 600*b*, and 600*c* can be configured in alternative arrangements and are not limited to the example embodiments described in this disclosure. Although not illustrated, the sensing devices 600*a*, 600*b*, and 600*c* may include wiring, a power source such as a battery, controller circuitry, and/or wireless communication circuitry. Accordingly, the sensing devices 600*a*, 600*b*, and 600*c* may receive power through the wiring, receive and process data through the controller circuitry, and transmit information through the wiring or the wireless communication circuitry.

Figure 6A:
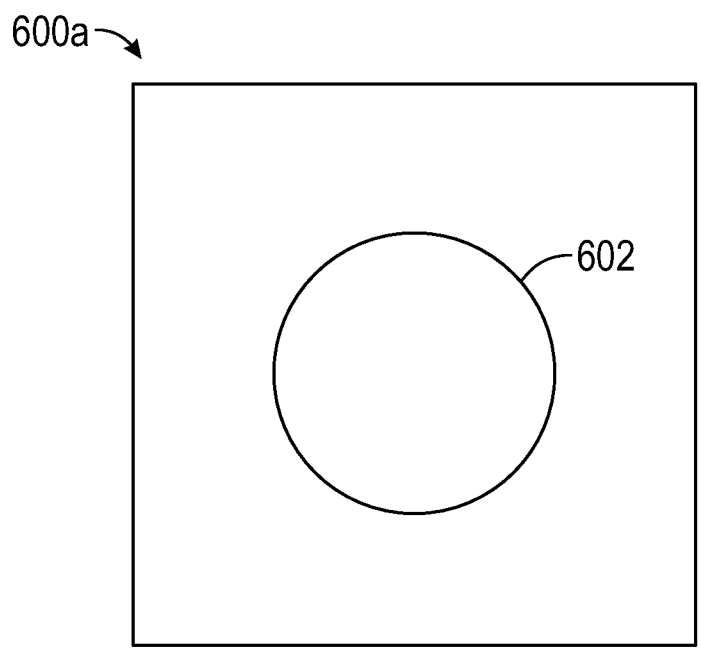
FIGS. 6A-6C generally illustrate example embodiments of sensing devices according to principles of the present disclosure.

FIG. 6A generally illustrates an example embodiment of a sensing device 600*a* according to the present disclosure. The sensing device 600*a* may be referred to as a temperature sensor or a temperature sensing device. In this regard, the sensing device 600*a* may include a temperature sensing element 602 (e.g., thermistor, transistor-based device, or the like) configured to detect data (e.g., environmental stimulus) associated with a user, and convert the data to (i.e., correlate the data with) a temperature of the user, and in particular, the temperate of a potential infected site of the user. The sensing device 600*a* can transmit the detected temperature information to the system 10, and the system 10 can use the detected temperature information to determine an infection probability of a potential infected site of the user and/or diagnose an infection of the user.

Also, the sensing device 600*a* can be used to detect a change (e.g., an increase or a decrease) in temperature of the user's body part, thereby indicating an increase or a decrease in the user's temperature. For example, the sensing device 600*a* can transmit, at different times, the temperature information to the system 10, and the system 10 can analyze and compare each instance of detected temperature information, and subsequently determine an increased user temperature, a decreased user temperature, or no change in user temperature. The system 10 can use the change in user temperature to determine an infection probability of a potential infected site of the user and/or diagnose the user for an infection.

Figure 6B:
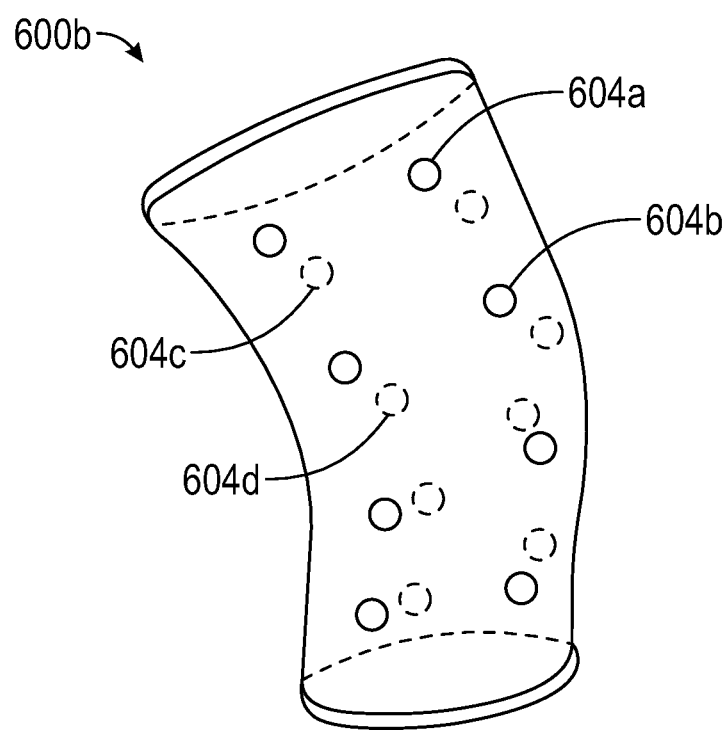

FIG. 6B generally illustrates an example embodiment of a sensing device 600*b* according to the present disclosure. The sensing device 600*b* may be referred to as a pressure sensor or a pressure sensing device. The sensing device 600*b* may include one or more pressure sensing elements (e.g., piezoelectric, strain gauge, diaphragm, or the like) configured to respond to pressure changes from a user. For example, as labeled in FIG. 6B, the sensing device 600*b* includes a pressure sensing element 604*a*, a pressure sensing element 604*b*, a pressure sensing element 604*c*, and pressure sensing element 604*d*. The pressure sensing elements, 604*a*, 604*b*, 604*c*, and 604*d*, as well as additional sensing elements (shown and not labeled), are positioned throughout various locations of the sensing device 600*b*. The respective locations of the sensing elements in FIG. 6B is exemplary, and other locations are possible. In some embodiments, the sensing device 600*b* includes a sleeve that can be fitted over a user's body part, such as a knee, an ankle, a shin, a thigh, an elbow, a bicep/triceps, a forearm, a wrist, or any other desired body part. The sensing device 600*b* may include an elastic or stretchable fabric, thereby providing a compression fit over the user's body part. When fitted onto the user's body part, the sensing device 600*b*, using the aforementioned pressure sensing elements, can detect swelling of the user's body part. For example, one or more of the aforementioned sensing elements of the sensing device 600*b* can respond to swelling of the user's body by bending or elastically deforming, and the amount or degree of bending or elastic deformation is proportional to the detected pressure. The sensing device 600b can transmit the pressure-related information to the system 10, and the system 10 can use the detected pressure information (e.g., average detected pressure of each of the pressure sensing elements, detected pressure of one or more specified pressure sensing elements) to determine an infection probability of a potential infected site of the user and/or diagnose the user for an infection.

Also, the sensing device 600b can be used to detect a change (e.g., an increase or a decrease) in swelling of the user's body part, thereby indicating increased swelling or decreased swelling. For example, the sensing device 600b can transmit, at different times, the detected pressure information to the system 10, and the system 10 can analyze and compare one or more instances of the detected pressure information, and subsequently determine an increased swelling, a decreased swelling, or no change in swelling. The system 10 can use the change in swelling to determine an infection probability of a potential infected site of the user and/or diagnose the user for an infection.

Figure 6C:
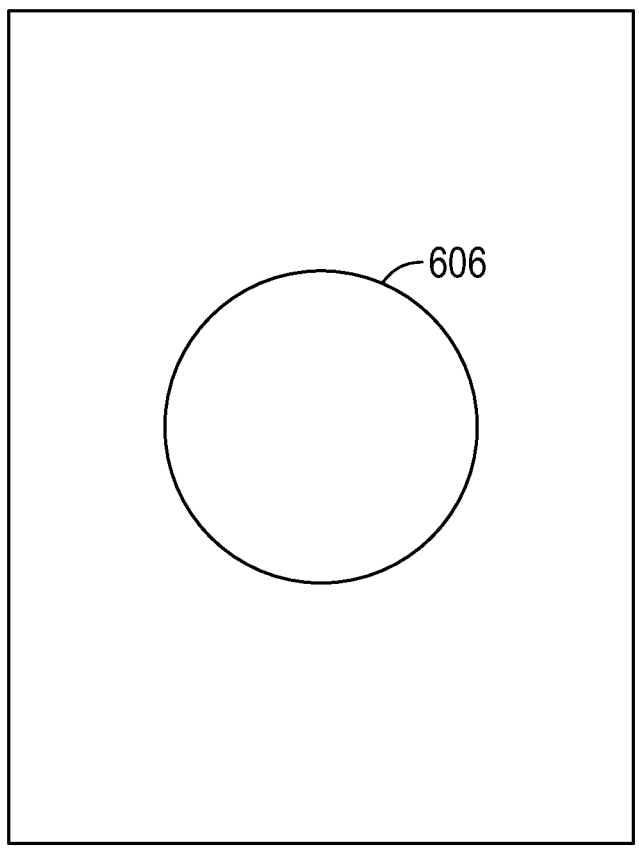

FIG. 6C generally illustrates an example embodiment of a sensing device 600c according to the present disclosure. The sensing device 600c may be referred to as a camera, an image sensor, an image capturing device, or an image sensing device. The sensing device 600c includes an image capturing element 606 (e.g., an optical module, lens, a charge-couple device ("CCD"), a complementary metal oxide semiconductor ("CMOS"), or some combination thereof) configured to capture data in the form of one or more images (e.g., still images or motion/video images) of a user. The data can be processed by the sensing device 600c to determine dimensional information of a breach in the user's skin due to an invasive procedure (e.g., surgery) or an accident incurred by the user, as non-limiting examples. The dimensional information may include one-dimensional information (e.g., a length) of the breach and/or two dimensional information (e.g., a surface) of the breach. Further, the dimensional information of the potential infected site may be directly proportional to the infection probability. In other words, the infection probability may be greater for relatively larger dimensional information, and conversely, the infection probability may be lesser for relatively smaller dimensional information. The sensing device 600c can transmit the dimensional information to the system 10, and the system 10 can use the dimensional information to determine an infection probability of a potential infected site of the user and/or diagnose the user for an infection.

Also, the sensing device 600c can be used to detect a change (e.g., an increase in a measurement or a decrease in a measurement) in the dimensional information of the breach. For example, the sensing device 600b can transmit, at different times, the dimensional information to the system 10, and the system 10 can analyze and compare one or more instances of the dimensional information, and subsequently determine an increased dimensional information, a decreased dimensional information, or no change in dimensional information. The system 10 can use the change in dimensional information to determine an infection probability of a potential infected site of the user and/or diagnose the user for an infection.

In addition to dimensional information, the data collected by the sensing device 600c can be analyzed for different purposes. For example, the sensing device 600c can capture images (e.g., motion/video images), and analyze the images to determine user mobility at the potential infected site. The increase in user mobility may be inversely proportional to the infection probability. In other words, the infection probability may increase or decrease with decreasing or increasing, respectively, user mobility at the potential infected site. As another example, the sensing device 600c can capture an image, and analyze the image to determine discoloration (e.g., redness of the skin, or other skin color abnormalities) of the user's skin at the potential infected site. The discoloration be directly proportional to the infection probability. In other words, the infection probability may increase or decrease with a measured amount of increasing or decreasing, respectively, discoloration at the potential infected site. As yet another example, the sensing device 600c can capture an image (e.g., still or motion/video images), and analyze the image to determine the temperature of the user at the potential infected site. Accordingly, in some embodiments, the sensing device 600c includes infrared sensing capabilities or any other desired sensing capabilities.

The system 10 can receive information from one or more of the sensors 600a, 600b, and 600c, and use the information to determine an infection probability of a potential infected site of the user and/or diagnose the user for an infection. Additionally, the system 10 can use information received from one the sensors 600a, 600b, and 600c to modify a treatment plan for the user. For example, the training engine 9 described in FIG. 1 can use information received by one or more of the sensors 600a, 600b, and 600c to train one or more machine learning models 13 to alter a treatment plan.

Figure 7:
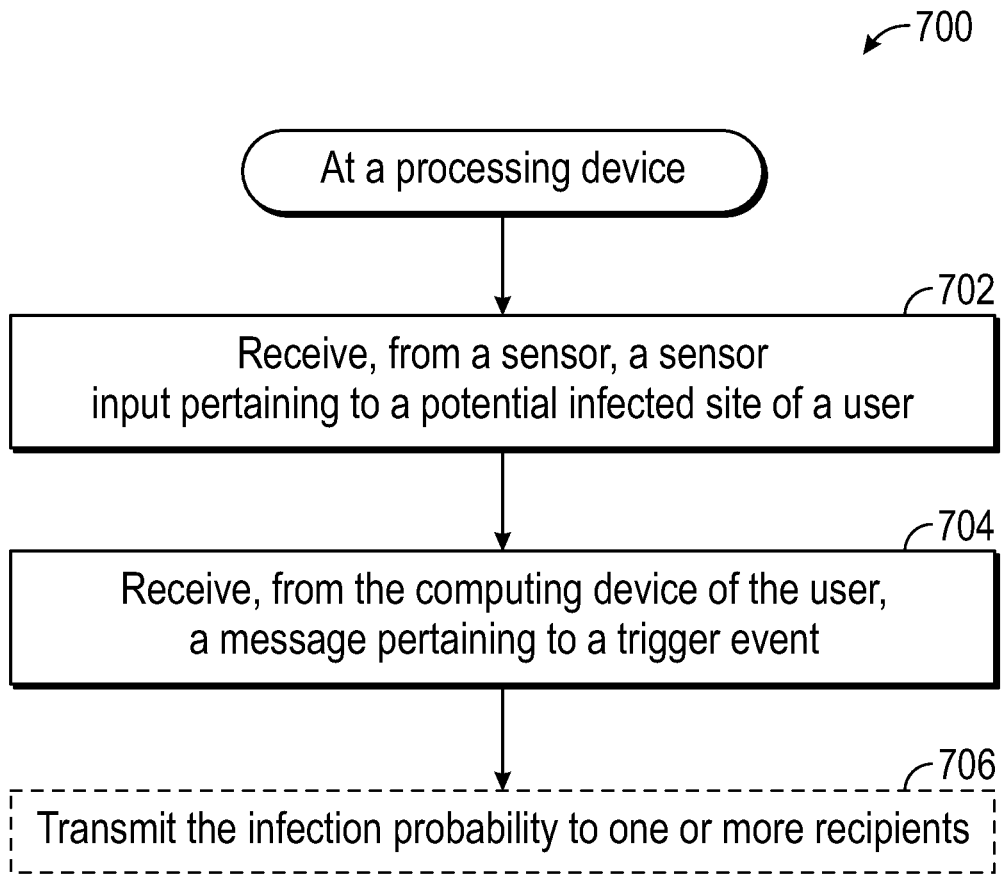
FIG. 7 generally illustrates a flow diagram illustrating a method for identifying, based on data received while a user uses the treatment device of FIG. 6A-6C, characteristics associated with a user infection according to principles of the present disclosure.

FIG. 7 generally illustrates an example embodiment of a method 700 for identifying characteristics associated with a user infection. The method 700 is performed by a processing device that may include hardware (circuitry, dedicated logic, etc.), software (such as is run on a general-purpose computer system or a dedicated machine), or a combination of both. The method 700 and/or each of its individual functions, routines, subroutines, or operations may be performed by one or more processors of a computing device (e.g., any component of FIG. 1, such as the server 30 executing the artificial intelligence engine 11). In certain implementations, the method 700 may be performed by a single processing thread. Alternatively, the method 700 may be performed by two or more processing threads, each thread implementing one or more individual functions, routines, subroutines, or operations of the methods.

For simplicity of explanation, the method 700 is depicted and described as a series of operations. However, operations in accordance with this disclosure can occur in various orders and/or concurrently, and/or with other operations not presented and described herein. For example, the operations depicted in the method 700 may occur in combination with any other operation of any other method disclosed herein. Furthermore, not all illustrated operations may be required to implement the method 700 in accordance with the disclosed subject matter. In addition, those skilled in the art will understand and appreciate that the method 700 could alternatively be represented as a series of interrelated states via a state diagram or events.

At step 702, the processing device receives, from a sensor, a sensor input pertaining to a potential infected site of a user. The sensor input may include an input, or signal, from a temperature sensor, a pressure sensor, and/or a camera described herein. Accordingly, the sensors shown and described in FIGS. 6A-6C may be integrated with the method 700. The sensor input may include characteristics such as temperature information, pressure information, discoloration information, image information, vital sign information, mobility information, and/or measurement information.

In addition to receiving a sensor input (or inputs), the processing device can also receive and use user input information. For example, the user information may include symptoms such as an indication of a pressure, an indication of a pain level, and/or an indication of a mobility. In order to provide the user input information to the processing device, a computing device (e.g., mobile device, desktop computer, laptop computer) with a user interface (e.g., a display of the computing device) can present a software application, or app.

At step 704, the processing device generates an infection probability associated with the infected site. The infection probability is based at least in part on the sensor input. Alternatively, or in combination, the infection probability is based on the user input information. The infection probability can be presented as a range (e.g., 0-10, 0%-100%), with an increasing value in the range indicating a relatively higher infection probability.

Optionally, at step 706, the infection probability can be transmitted to one or more recipients. For example, the infection probability can be transmitted to the user, a medical professional, an insurance provider, and/or a healthcare administrator. Once received, a telemedicine-enabled appointment can be scheduled between the user and one or more of the medical professional, the insurance provider, and/or the healthcare administrator. The telemedicine-enabled appointment allows the user to remotely receive communication (e.g., the treatment plan) from any of the medical professional, the insurance provider, and/or the healthcare administrator. In other words, by using the telemedicine-enabled appointment, the user is not required to make an in-office visit and does need to be in physical proximity to (i.e., not in the same room or building as) the medical professional, the insurance provider, and/or the healthcare administrator. By transmitting the infection probability during instances when the infection probability is at least at a threshold infection probability, some appointments may be avoided when the infection probability is sufficiently low (i.e., below the threshold infection probability). However, it should be noted that in some embodiments, the infection probability can be transmitted the medical professional, the insurance provider, and/or the healthcare administrator, even when the infection probability is below the threshold infection probability.

In some embodiments, the infection probability is transmitted when the infection probability is at least (i.e., equals or exceeds) at a threshold infection probability. The processing device can receive or identify the threshold infection probability, which may correspond to a particular infection or a risk level of infection that requires a treatment plan. Different risk levels of infection can be assigned to different users based upon one or more factors, including, but not limited to, the user's age, the user's medical history (e.g., an immunocompromised user, a user with little or no prior medical issues), the type of infection identified, and/or the known ability for a medication to effectively treat an infection. Accordingly, the threshold infection probability can vary for each user based upon a variety of factors. Moreover, for the same type of infection, users with a relatively high risk level (e.g., an older user with prior medical issues) may be assigned a relatively lower threshold infection probability, as compared to user s with a relatively high risk level (e.g., a younger user with no prior medical issues). As a result, in some instances, the infection probability is more likely to reach at least the threshold infection probability for user s with a relatively high risk level. In this regard, the method 700 may provide a more efficient method for a medical professional, an insurance provider, and/or a healthcare administrator to interact with user s.

In some embodiments, the processing device receives or identifies multiple the threshold infection probabilities, with each threshold infection probability corresponding to a particular risk level. For example, when the processing device receives or identifies a first threshold infection probability and a second threshold probability, the first threshold infection probability may correspond to a relatively low risk level while the second threshold infection probability may correspond to a relatively high risk level. In this regard, the first threshold infection probability may indicate that the user should seek a treatment plan for the potential infected site, while the second threshold infection probability may indicate that the user should seek immediate treatment for the potential infected site or immediately set up a telemedicine-enabled appointment with a medical professional. Accordingly, the processing device can compare the infection probability with multiple threshold infection probabilities, and provide multiple ways to treat an infection based on the associated risk level.

The processing device can use the characteristics to diagnose the potential infected site. For example, using one or more of the sensor input and the user input information, the processing device may determine a type of infection (e.g., a bacterial infection such as a Staph infection caused by *staphylococcus* bacteria, a germ, a parasite, a virus, or some combination thereof) associated with the potential infected site. Moreover, based on the diagnosis, the processing device can recommend a treatment plan to the user. The diagnosis and/or the treatment plan can be transmitted to the user. In some embodiments, the diagnosis and/or the treatment plan is first transmitted to the medical professional, the insurance provider, and/or the healthcare administrator for review, and once approved, is transmitted to the user.

Alternatively, or in combination, the processing device can receive and use etiological information associated with the potential infected site to determine an infection probability and/or diagnose an infection. For example, the processing device can receive information indicating that the user has undergone an invasive operation event (e.g., a surgical procedure) at the potential infected site, thereby indicating the type of incision made to the user. In another example, the processing device can receive information indicating that the user has undergone an injury event (e.g., an accident) at the potential infected site, thereby indicating the user has an open wound or a cut.

Additionally, the processing device can receive multiple sensor inputs to determine an infection probability. For example, the processing device can receive a first input at a potential infected site and a second input from a non-infected site. A "non-infection site" may refer to, for example, no statistical probability of infection). The processing device can compare the first input with the second input to generate the infection probability. This may include, for example, a comparison between a first temperature (from the first input) at the potential infected site (e.g., a user's left knee), and a second temperature (from the second input) at the non-infected site (e.g., a user's right knee). In some embodiments, the processing device analyzes the comparison to determine the infection probability. For example, the difference between the first temperature and the second temperature can be directly proportional to the infection probability, and accordingly, the processing device determines a relatively high infection probability for a larger difference (e.g., 3 degrees on a Celsius or Fahrenheit scale) between the first temperature and the second temperature, and conversely, the processing device determines a relatively low infection probability for a smaller difference (e.g., 0.5 degrees on a Celsius or Fahrenheit scale) between the first temperature and the second temperature. Alternatively, or in combination, the processing device can use a predetermined difference between the first temperature and the second temperature to determine the infection probability. For example, in some embodiments, the processing device may require the difference between the first temperature and the second temperature be at least a specified difference (e.g., 2 degrees on a Celsius or Fahrenheit scale), as oppose to the first temperature simply being greater than the second temperature. In this regard, the processing device may determine the infection probability with increased accuracy and/or prevent or limit "false positives" with respect to determine the presence of an infection.

Figure 8:
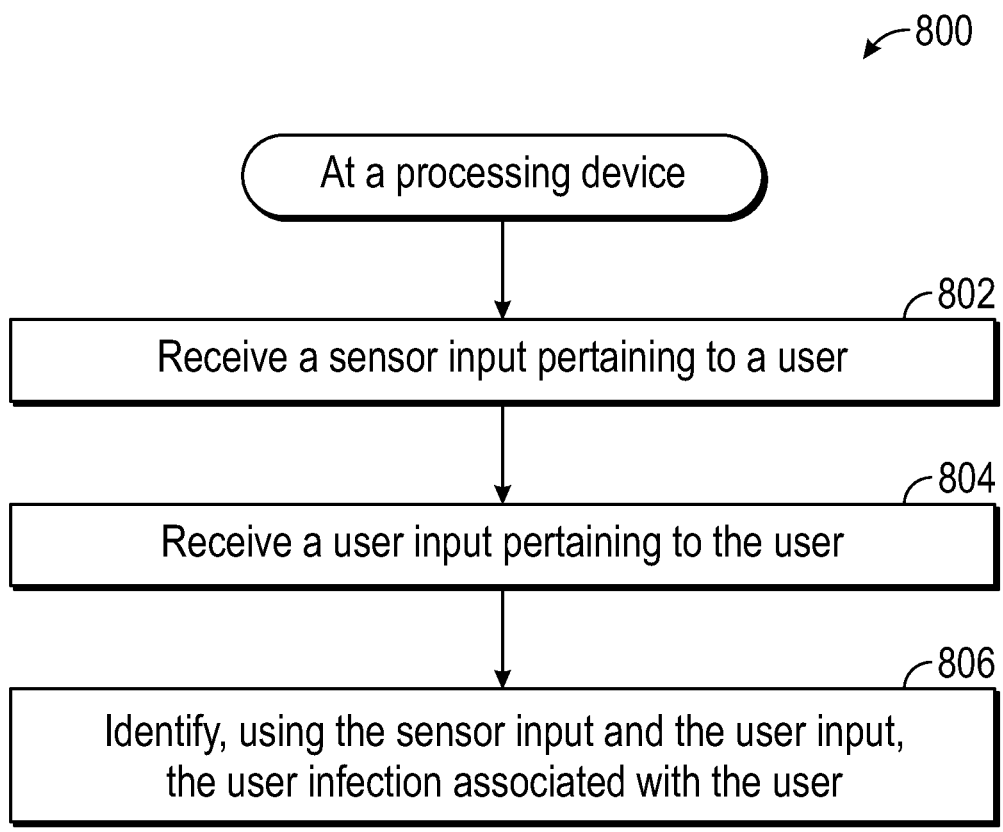
FIG. 8 generally illustrates a flow diagram illustrating a method for diagnosing a user infection based on one or more identifying characteristics associated with a user infection according to principles of the present disclosure.

FIG. 8 generally illustrates an example embodiment of a method 800 for diagnosing a user based on one or more identifying characteristics associated with a user infection according to principles of the present disclosure. The method 800 is performed by processing logic that may include hardware (circuitry, dedicated logic, etc.), software (such as is run on a general-purpose computer system or a dedicated machine), or a combination of both. The method 800 and/or each of its individual functions, routines, subroutines, or operations may be performed by one or more processors of a computing device (e.g., any component of FIG. 1, such as server 30 executing the artificial intelligence engine 11). In certain implementations, the method 800 may be performed by a single processing thread. Alternatively, the method 800 may be performed by two or more processing threads, each thread implementing one or more individual functions, routines, subroutines, or operations of the methods.

At step 802, the processing device receives, from a sensor, a sensor input pertaining to a potential infected site of a user. The sensor input from the sensor may include an input from a temperature sensor, a pressure sensor, or a camera described herein. Accordingly, the sensor input may include characteristics such as temperature information, pressure information, discoloration information, image information, vital sign information, or measurement information.

At step 804, the processing device receives a user input. The user input information may be provided by the user, either from the user to the processing device via computing system or indirectly via a medical professional, the insurance provider, and/or the healthcare administrator. The user input may include symptoms such as an indication of a pressure, an indication of a pain level, and an indication of a mobility.

At step 806, the processing device identifies, using the sensor input and the user input, the user infection associated with the user. In some embodiments, the sensor input and/or the user input is used to identify the user infection.

Additionally, the processing device can receive and use etiological information associated with the user. For example, the processing device can receive information indicating the user has undergone an invasive operation event (e.g., surgical procedure) at the potential infected site, thereby indicating the type of incision to the user. In another example, the processing device can receive information indicating the user has undergone an injury event (e.g., accident) at the potential infected site, thereby indicating the user has an open wound or a cut.

When the user infection is identified, the processing device can initiate additional steps. For example, the processing device can generate a recommendation for one or more of a medication, a treatment plan, and a visit with a medical professional. In the case of the visit with the medical professional, a telemedicine-enabled appointment can be scheduled between the user and the medical professional.

Figure 9:
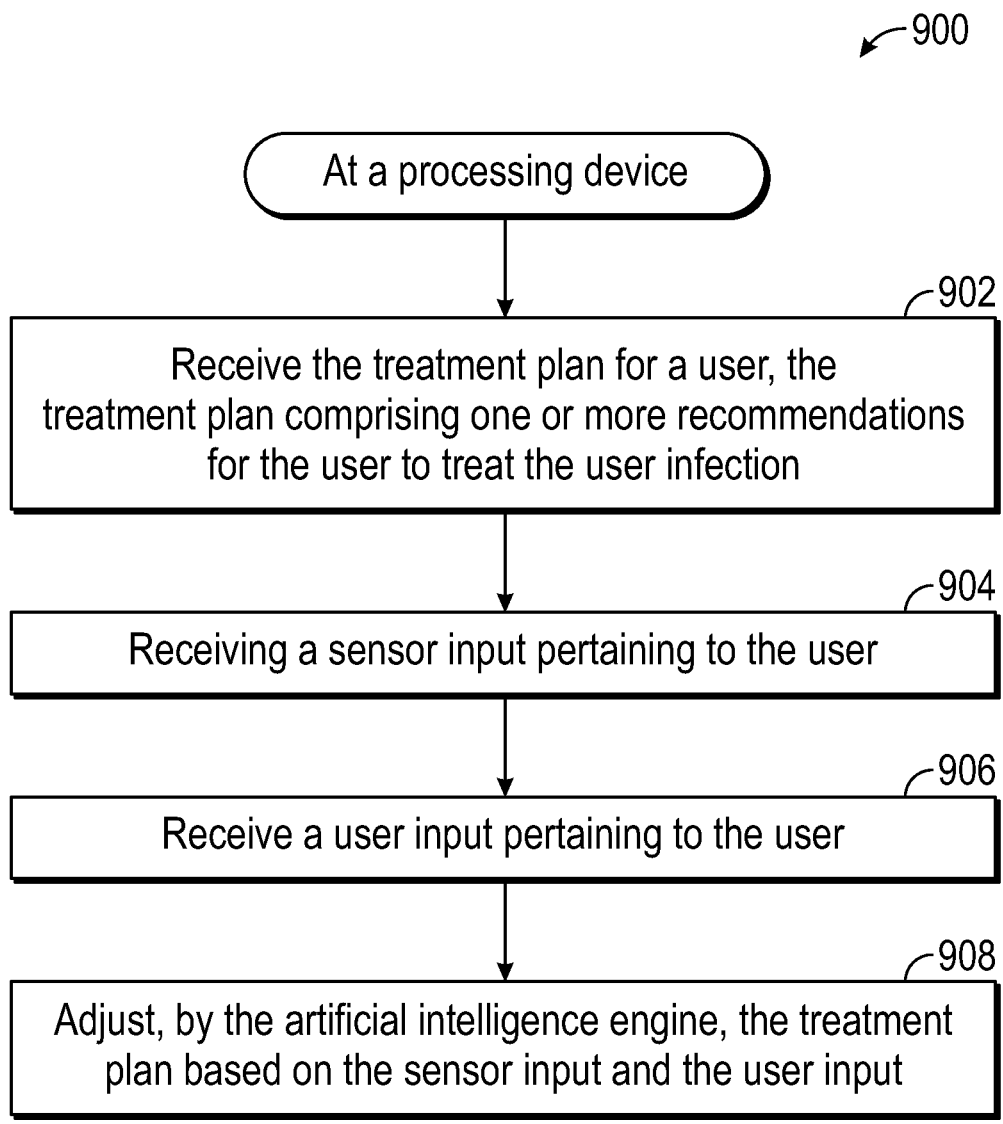
FIG. 9 generally illustrates a flow diagram illustrating a method for modifying, by an artificial intelligence engine, a treatment plan for optimizing an outcome for a user infection according to principles of the present disclosure.

FIG. 9 generally illustrates an example embodiment of a method 900 for modifying, by an artificial intelligence engine, a treatment plan for optimizing an outcome for a user infection according to principles of the present disclosure. The method 900 is performed by processing logic that may include hardware (circuitry, dedicated logic, etc.), software (such as is run on a general-purpose computer system or a dedicated machine), or a combination of both. The method 900 and/or each of its individual functions, routines, subroutines, or operations may be performed by one or more processors of a computing device (e.g., any component of FIG. 1, such as server 30 executing the artificial intelligence engine 11). In certain implementations, the method 900 may be performed by a single processing thread. Alternatively, the method 900 may be performed by two or more processing threads, each thread implementing one or more individual functions, routines, subroutines, or operations of the methods.

At step 902, the treatment plan for the user is received. For example, the processing device may receive treatment plan from the user's medical professional. The treatment plan may include one or more recommendations for the user to treat the user infection. For example, the treatment plan may include a medication, and/or a visit with a medical professional. In the case of the visit with the medical professional, a telemedicine-enabled appointment can be scheduled between the user and the medical professional.

At step 904, the processing device receives, from a sensor, a sensor input pertaining to a potential infected site of a user. The sensor input from the sensor may include an input from a temperature sensor, a pressure sensor, or a camera described herein. Accordingly, the sensor input may include characteristics such as temperature information, pressure information, discoloration information, image information, vital sign information, measurement information, any other desired information, or combination thereof.

At step 906, the processing device receives a user input. In some embodiments, the user provides the user input through a computing system (e.g., a mobile device, a tablet device, a laptop computing device, a desktop computing device) with a user interface (e.g., a display) running a software application, or app, on the user interface. In some embodiments, the user provides the user input indirectly via a medical professional, the insurance provider, and/or the healthcare administrator. The user input may include symptoms such as an indication of a pressure, an indication of discoloration, an indication of a pain level, and/or an indication of a mobility.

At step 908, the artificial intelligence engine uses the sensor input and the user input to adjust the treatment plan. For example, a treatment plan may include different types of medications, with each type of medication designed to treat different risk level and/or severities. When the processing device receives a treatment plan that recommends a first medication associated with a relatively low risk level or relatively low severity of a user infection, the artificial intelligence engine may use the sensor input and the user input to adjust the treatment plan and subsequently recommend a second medication associated with a relatively high risk level or relatively high severity of a user infection. Conversely, when the processing device receives a treatment plan that recommends the second medication, the artificial intelligence may adjust the treatment plan, based on the sensor input and the user input, and subsequently recommend the first medication. Accordingly, the artificial intelligence engine can modify the medication based on an increasing or decreasing risk/severity level.

In addition to adjusting the type of medication, the artificial intelligence engine can adjust treatment plans in other ways. For example, a treatment plan may include a recommended frequency of application of a medication, a recommendation to rest or immobilize the user (e.g., at the user infection site), and/or a recommendation to wrap/cover the user infection. The additional ways for adjusting the treatment plan can be modified by the artificial intelligence engine to account for a change in risk level or severity of a user infection. For example, when one or more of the sensor input and the user input provide(s) an indication of a decreased risk level or decreased severity of the patient infection, the artificial intelligence engine may adjust the treatment plan, and subsequently recommend a decreased application frequency of the medication, and/or a reduction in covering/wrapping the user infection. Conversely, when one or more of the sensor input and the user input provide(s) an indication of an increased risk level or increased severity of the user infection, the artificial intelligence engine may adjust the treatment plan, and subsequently recommend an increased application frequency of the medication, a recommendation for the user to rest, and/or a recommendation to cover/wrap the user infection. Accordingly, the artificial intelligence engine can modify the treatment plan, based on an increasing or decreasing risk/severity level, to adapt to real-time characteristics of the user.

Figure 10:
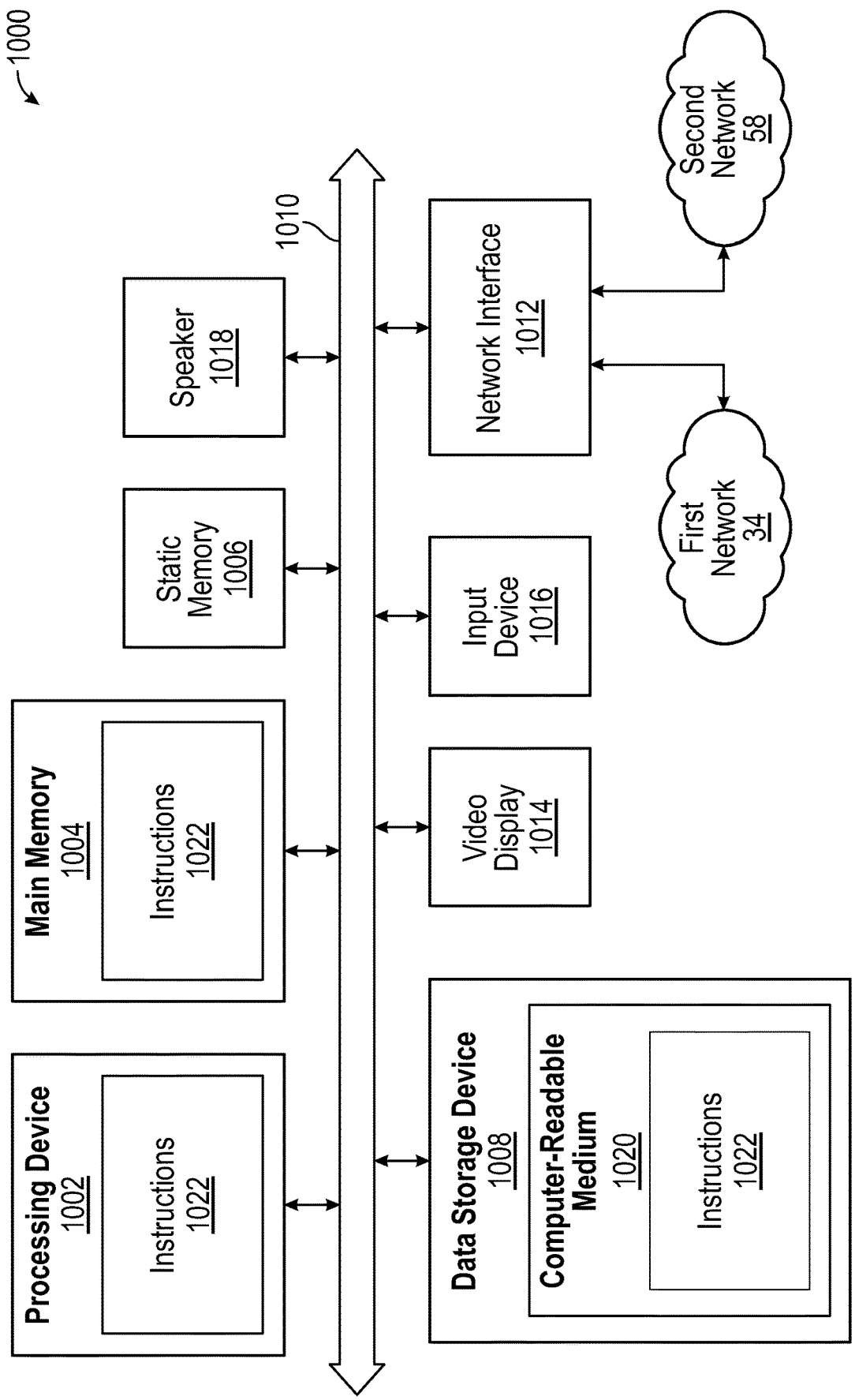
FIG. 10 generally illustrates a computer system according to principles of the present disclosure.

FIG. 10 generally illustrates a computer system 1000 according to principles of the present disclosure. In one example, computer system 1000 may include a computing device and correspond to the assistance interface 94, reporting interface 92, supervisory interface 90, clinician interface 20, server 30 (including the AI engine 11), user interface 50, ambulatory sensor 82, goniometer 84, treatment apparatus 70, pressure sensor 86, or any suitable component of FIG. 1. The computer system 1000 may be capable of executing instructions implementing the one or more machine learning models 13 of the artificial intelligence engine 11 of FIG. 1. The computer system may be connected (e.g., networked) to other computer systems in a LAN, an intranet, an extranet, or the Internet, including via the cloud or a peer-to-peer network. The computer system may operate in the capacity of a server in a client-server network environment. The computer system may be a personal computer (PC), a tablet computer, a wearable (e.g., wristband), a set-top box (STB), a personal Digital Assistant (PDA), a mobile phone, a camera, a video camera, an Internet of Things (IoT) device, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 1000 includes a processing device 1002, a main memory 1004 (e.g., read-only memory (ROM), flash memory, solid state drives (SSDs), dynamic random access memory (DRAM) such as synchronous DRAM (SDRAM), a static memory 1006 (e.g., flash memory, solid state drives (SSDs), static random access memory (SRAM), and a data storage device 1008, which communicate with each other via a bus 1010.

Processing device 1002 represents one or more general-purpose processing devices such as a microprocessor, central processing unit, or the like. More particularly, the processing device 1002 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1402 may also be one or more special-purpose processing devices such as an application specific integrated circuit (ASIC), a system on a chip, a field programmable gate array (FPGA), a digital signal processor (DSP), network processor, or the like. The processing device 1402 is configured to execute instructions for performing any of the operations and steps discussed herein.

The computer system 1000 may further include a network interface device 1012. The computer system 1000 also may include a video display 1014 (e.g., a liquid crystal display (LCD), a light-emitting diode (LED), an organic light-emitting diode (OLED), a quantum LED, a cathode ray tube (CRT), a shadow mask CRT, an aperture grille CRT, a monochrome CRT), one or more input devices 1016 (e.g., a keyboard and/or a mouse or a gaming-like control), and one or more speakers 1018 (e.g., a speaker). In one illustrative example, the video display 1014 and the input device(s) 1016 may be combined into a single component or device (e.g., an LCD touch screen).

The one or more input devices 1016 may include a computer-readable storage medium 1020 on which the instructions 1022 embodying any one or more of the methods, operations, or functions described herein is stored. The instructions 1022 may also reside, completely or at least partially, within the main memory 1004 and/or within the processing device 1002 during execution thereof by the computer system 1000. As such, the main memory 1004 and the processing device 1002 also constitute computer-readable media. The instructions 1022 may further be transmitted or received over a network via the network interface device 1012.

While the computer-readable storage medium 1020 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

Consistent with the above disclosure, the examples of systems and method enumerated in the following clauses are specifically contemplated and are intended as a non-limiting set of examples.

Clause 1. A system for identifying a condition of a user, the system comprising:

a treatment apparatus configured to be manipulated by the user for performing an exercise;

an interface communicably coupled to the treatment apparatus;

one or more sensors configured to sense one or more characteristics of an anatomical structure of the user; and a processing device and a memory communicatively coupled to the processing device, and the memory includes computer readable instructions that, when executed by the processing device, cause the processing device to:

receive, from the sensors, one or more sensor inputs representative of the one or more of characteristics of the anatomical structure;

calculate an infection probability of a disease based on the one or more characteristics of the anatomical structure; and output, to the interface, a representation of the infection probability.

Clause 2. The system of any clause herein, wherein the processing device is further configured to identify, one or more characteristics associated with the anatomical structure that is diseased.

Clause 3. The system of any clause herein, wherein the processing device is further configured to diagnose, based on the one or more characteristics, a presence of the disease and wherein the infection probability correlates with the probability of the disease being diagnosed by a medical professional.

Clause 4. The system of any clause herein, wherein the processing device is further configured to output, to the interface, a recommendation for a treatment plan based on at least one of the infection probability and the diagnosis.

Clause 5. The system of any clause herein, wherein the interface is configured to present at least one of an image or an audible or tactile signal representative of the infection probability.

Clause 6. The system of any clause herein, wherein the processing device is further configured to:

selectively identify a threshold infection probability; and selectively identify the infection probability being at least equal to the threshold infection probability.

Clause 7. The system of any clause herein, wherein the interface is associated with one or more of the treatment apparatus and a medical professional.

Clause 8. The system of any clause herein, wherein the processing device is further configured to output, to the interface, a recommendation for one or more of a medication, a treatment plan, and a visit with a medical professional.

Clause 9. The system of any clause herein, wherein the visit comprises a telemedicine-enabled appointment, the telemedicine-enabled appointment characterized by the medical professional and the user not being in direct physical proximity to each other.

Clause 10. The system of any clause herein, wherein the disease is defined as an infection related to one of a surgical site or injury of the anatomical structure.

Clause 11. The system of any clause herein, wherein the processing device is further configured to:

receive, from the interface, one or more inputs; and generate, based on one or more of the one or more inputs and the one or more sensor inputs, the infection probability.

Clause 12. The system of any clause herein, wherein the one or more inputs comprise one or more of an indication, associated with the user, of a pressure, a pain level, discoloration of a structure, and a mobility of a structure.

Clause 13. The system of any clause herein, wherein the one or more characteristics are defined as one or more etiological characteristics, and the processing device is further configured to generate the infection probability based on the one or more etiological characteristics.

Clause 14. The system of any clause herein, wherein the one or more etiological characteristics comprise at least one of a procedure or injury associated with the structure.

Clause 15. The system of an clause herein, wherein the one or more sensor inputs comprises one or more of temperature information, pressure information, discoloration information, image information, vital sign information, or measurement information.

Clause 16. The system of any clause herein, wherein the processing device is further configured to:

generate, from the one or more characteristics, a baseline characteristic and a disease characteristic; and generate the infection probability based on the one or more characteristics, the baseline characteristic and the disease characteristic.

Clause 17. The system of any clause herein, wherein the baseline characteristic represents a state of the anatomical structure without the disease characteristic.

Clause 18. A method for identifying a condition, the method comprising:

receiving, from one or more sensors, one or more sensor inputs representative of one or more of characteristics of an anatomical structure;

calculating an infection probability of a disease based on the one or more characteristics of the anatomical structure; and outputting, to an interface, a representation of the infection probability.

Clause 19. The method of any clause herein, further comprising identifying one or more characteristics associated an anatomical structure having the diseased characteristics.

Clause 20. The method of any clause herein, further comprising diagnosing, based on the one or more characteristics, a presence of a disease and wherein the infection probability correlates with the probability of the disease being diagnosed by a medical professional.

Clause 21. The method of any clause herein, further comprising presenting, in the interface, a recommendation for a treatment plan based on at least one of the infection probability and the diagnosis.

Clause 22. The method of any clause herein, further comprising presenting, with the interface, at least one of an image and an audible or tactile signal representative of the infection probability.

Clause 23. The method of any clause herein, further comprising:

identifying a threshold infection probability;

identifying the infection probability being at least equal to the threshold infection probability; and presenting, in the interface, the infection probability.

Clause 24. The method of any clause herein, further comprising presenting, in the interface, a recommendation for one or more of a medication, a treatment plan, and a visit with a medical professional.

Clause 25. The method of any clause herein, wherein the visit comprises a telemedicine-enabled appointment, the telemedicine-enabled appointment defined by the medical professional and the user not being in direct physical proximity to each other.

Clause 26. The method of any clause herein, further comprising:

receiving, from the interface, one or more inputs; and generating, based on one or more of the one or more inputs and the one or more sensor inputs, the infection probability.

Clause 27. A system for identifying a condition of a user, the system comprising:

a treatment apparatus configured to be manipulated by the user for performing an exercise;

one or more sensors configured to sense one or more characteristics of an anatomical structure of the user; and a processing device and a memory communicatively coupled to the processing device and the memory includes computer readable instructions that, when executed by the processing device, cause the processing device to:

receive, from the sensors, one or more sensor inputs representative of the one or more of characteristics of the anatomical structure;

generate, from the one or more characteristics, a baseline characteristic and a disease characteristic; and generate an infection probability of a disease based on the one or more characteristics, the baseline characteristic and the disease characteristic.

Clause 28. The system of any clause herein, further comprising an interface communicatively coupled to the treatment apparatus, and wherein the processing device is further configured to:

receive, from the interface, one or more inputs; and generate the infection probability based on one or more of the one or more inputs and the one or more sensor inputs.

Clause 29. The system of any clause herein, further comprising an interface communicatively coupled to the treatment apparatus, and wherein the processing device is further configured to:

selectively identify a threshold infection probability;

selectively identify the infection probability being at least equal to the threshold infection probability; and output, to the interface, a representation of the infection probability when the infection probability is at least equal to the threshold infection probability.

Clause 30. The system of any clause herein, wherein the processing device is further configured to:

identify one or more diseased characteristics associated with the anatomical structure;

identify, based on the one or more diseased characteristics, the infection probability; and diagnose, based on the one or more diseased characteristics, a presence of a disease of the anatomical structure.

Many of the electrical connections in the drawings are shown as direct couplings having no intervening devices, but not expressly stated as such in the description above. Nevertheless, this paragraph shall serve as antecedent basis in the claims for referencing any electrical connection as "directly coupled" for electrical connections shown in the drawing with no intervening device(s).

Various functions described below can be implemented or supported by one or more computer programs, each of which is formed from computer readable program code and embodied in a computer readable storage medium. The terms "application" and "program" refer to one or more computer programs, software components, sets of instructions, procedures, functions, methods, objects, classes, instances, related data, or a portion thereof adapted for implementation in a suitable computer readable program code. The phrase "computer readable program code" includes any type of computer code, including source code, object code, and executable code. The phrase "computer readable storage medium" includes any type of medium capable of being accessed by a computer, such as read only memory (ROM), random access memory (RAM), a hard disk drive, a flash drive, a compact disc (CD), a digital video disc (DVD), solid state drive (SSD), or any other type of memory. A "non-transitory" computer readable storage medium excludes wired, wireless, optical, or other communication links that transport transitory electrical or other signals. A non-transitory computer-readable storage medium includes media where data can be permanently stored and media where data can be stored and later overwritten, such as a rewritable optical disc or an erasable memory device.

The above discussion is meant to be illustrative of the principles and various embodiments of the present invention. Once the above disclosure is fully appreciated, numerous variations and modifications will become apparent to those skilled in the art. It is intended that the following claims be interpreted to embrace all such variations and modifications.

What is claimed is:

1. A system comprising:

a treatment apparatus configured to be manipulated by the user for performing an exercise;

an interface communicatively coupled to the treatment apparatus;

one or more sensors configured to sense one or more characteristics of an anatomical structure of the user; and a processing device and a memory communicatively coupled to the processing device, and the memory includes computer readable instructions that, when executed by the processing device, cause the processing device to:

receive, from the sensors, one or more sensor inputs describing the one or more characteristics of the anatomical structure related to a current status of the user;

calculate an infection probability of a disease based on the one or more characteristics of the anatomical structure;

output for display, on the interface, a visual representation of the infection probability; and output for display, on the interface, a recommendation for a treatment plan, the treatment plan comprising information related to the user's performance of the exercise via the treatment apparatus, the exercise corresponding to the disease.

2. The system of claim 1, wherein the processing device is further configured to identify, one or more characteristics associated with the anatomical structure that is diseased.

3. The system of claim 2, wherein the processing device is further configured to diagnose, based on the one or more characteristics, a presence of the disease and wherein the infection probability correlates with the probability of the disease being diagnosed by a medical professional.

4. The system of claim 3, wherein the treatment plan is based on at least one of the infection probability and the diagnosis.

5. The system of claim 1, wherein the interface is configured to present at least one of an image or an audible or tactile signal representative of the infection probability.

6. The system of claim 1, wherein the processing device is further configured to:

selectively identify a threshold infection probability; and selectively identify the infection probability being at least equal to the threshold infection probability.

7. The system of claim 6, wherein the interface is associated with one or more of the treatment apparatus and a medical professional.

8. The system of claim 6, wherein the processing device is further configured to output, to the interface, a recommendation for one or more of a medication and making an appoint to see a medical professional.

9. The system of claim 8, wherein the visit comprises a telemedicine-enabled appointment, the telemedicine-enabled appointment characterized by the medical professional and the user not being in direct physical proximity to each other.

10. The system of claim 1, wherein the disease is defined as an infection related to one of a surgical site or injury of the anatomical structure.

11. The system of claim 1, wherein the processing device is further configured to:
receive, from the interface, one or more inputs; and
generate, based on one or more of the one or more inputs and the one or more sensor inputs, the infection probability.

12. The system of claim 11, wherein the one or more inputs comprise one or more of an indication, associated with the user, of a pressure, a pain level, discoloration of a structure, and a mobility of a structure.

13. The system of claim 1, wherein the one or more characteristics are defined as one or more etiological characteristics, and the processing device is further configured to generate the infection probability based on the one or more etiological characteristics.

14. The system of claim 13, wherein the one or more etiological characteristics comprise at least one of a procedure or injury associated with the structure.

15. The system of claim 1, wherein the one or more sensor inputs comprises one or more of temperature information, pressure information, discoloration information, image information, vital sign information, or measurement information.

16. The system of claim 1, wherein the processing device is further configured to:
generate, from the one or more characteristics, a baseline characteristic and a disease characteristic; and
generate the infection probability based on the one or more characteristics, the baseline characteristic and the disease characteristic.

17. The system of claim 16, wherein the baseline characteristic represents a state of the anatomical structure without the disease characteristics.

18. A method comprising:
receiving, from one or more sensors, one or more sensor inputs describing one or more characteristics of an anatomical structure of a user, the one or more characteristics corresponding to a current status of the user;
calculating an infection probability of a disease based on the one or more characteristics of the anatomical structure;
outputting for display, on an interface, a visual representation of the infection probability; and
outputting for display, on the interface, a recommendation for a treatment plan, the treatment plan comprising information related to the user's performance of an exercise via a treatment apparatus, the exercise corresponding to the disease.

19. The method of claim 18, further comprising identifying one or more characteristics associated with a diseased anatomical structure.

20. The method of claim 19, further comprising diagnosing, based on the one or more characteristics, a presence of a disease and wherein the infection probability correlates with the probability of the disease being diagnosed by a medical professional.

21. The method of claim 20, wherein the treatment plan is based on at least one of the infection probability and the diagnosis.

22. The method of claim 18, further comprising presenting, with the interface, at least one of an image and an audible or tactile signal representative of the infection probability.

23. The method of claim 18, further comprising:
identifying a threshold infection probability;
identifying the infection probability being at least equal to the threshold infection probability; and
presenting, in the interface, the infection probability.

24. The method of claim 23, further comprising presenting, in the interface, a recommendation for one or more of a medication and making an appointment to see a medical professional.

25. The method of claim 24, wherein the visit comprises a telemedicine-enabled appointment, the telemedicine-enabled appointment defined by the medical professional and a user not being in direct physical proximity to each other.

26. The method of claim 18, further comprising:
receiving, from the interface, one or more inputs; and
generating, based on one or more of the one or more inputs and the one or more sensor inputs, the infection probability.

27. A system comprising:
a treatment apparatus configured to be manipulated by the user for performing an exercise;
one or more sensors configured to sense one or more characteristics of an anatomical structure of the user; and
a processing device and a memory communicatively coupled to the processing device and the memory includes computer readable instructions that, when executed by the processing device, cause the processing device to:
receive, from the sensors, one or more sensor inputs describing the one or more characteristics of the anatomical structure related to a current status of the user;
generate, from the one or more characteristics, a baseline characteristic and a disease characteristic;
generate an infection probability of a disease based on the one or more characteristics, the baseline characteristic and the disease characteristic; and
generate, for display on a display associated with the processing device, a recommendation for a treatment plan, the treatment plan comprising information related to the user's performance of the exercise via the treatment apparatus, the exercise corresponding to the disease.

28. The system of claim 27, further comprising an interface communicatively coupled to the treatment apparatus, and wherein the processing device is further configured to:
receive, from the interface, one or more inputs; and
generate the infection probability based on one or more of the one or more inputs and the one or more sensor inputs.

29. The system of claim 27, further comprising an interface communicatively coupled to the treatment apparatus, and wherein the processing device is further configured to:
selectively identify a threshold infection probability;
selectively identify the infection probability being at least equal to the threshold infection probability; and
output, to the interface, a representation of the infection probability when the infection probability is at least equal to the threshold infection probability.

30. The system of claim 27, wherein the processing device is further configured to:
identify one or more diseased characteristics associated with an anatomical structure;
identify, based on the one or more diseased characteristics, the infection probability; and diagnose, based on the one or more diseased characteristics, a presence of a disease of the anatomical structure.

\* \* \* \* \*